United States Patent
Skead et al.

(10) Patent No.: US 10,927,113 B2
(45) Date of Patent: Feb. 23, 2021

(54) PROCESS FOR PREPARING PURINE DERIVATIVES

(71) Applicant: Cyclacel Limited, London (GB)

(72) Inventors: Benjamin Mark Skead, Cambridge (GB); Robert Westwood, Oxon (GB); Derek Londesbrough, Hartlepool (GB); Julian Scott Northen, South Shields (GB); Jonathan Charles Christian Atherton, Durham (GB)

(73) Assignee: Cyclacel Limited, London (GB)

(*) Notice: Subject to any disclaimer, the term of this patent is extended or adjusted under 35 U.S.C. 154(b) by 0 days.

(21) Appl. No.: 16/480,858

(22) PCT Filed: Jan. 25, 2018

(86) PCT No.: PCT/GB2018/050208
§ 371 (c)(1),
(2) Date: Jul. 25, 2019

(87) PCT Pub. No.: WO2018/138500
PCT Pub. Date: Aug. 2, 2018

(65) Prior Publication Data
US 2019/0389863 A1    Dec. 26, 2019

(30) Foreign Application Priority Data

Jan. 26, 2017  (GB) .................................. 1701318.6
Jan. 26, 2017  (GB) .................................. 1701319.4
(Continued)

(51) Int. Cl.
*C07D 473/16*    (2006.01)
*C07D 473/40*    (2006.01)

(52) U.S. Cl.
CPC ......... *C07D 473/16* (2013.01); *C07D 473/40* (2013.01)

(58) Field of Classification Search
CPC .................................................. C07D 473/16
See application file for complete search history.

(56) References Cited

U.S. PATENT DOCUMENTS 7,582,642 B2   9/2009   Fischer et al.
8,592,581 B2   11/2013  Sheldrake et al.
(Continued)

FOREIGN PATENT DOCUMENTS

WO    2003002565 A1   1/2003
WO    2008122767 A2   10/2008
(Continued)

OTHER PUBLICATIONS

Gellis A. et al., "Synthesis and cytotoxicity evaluation of some benzimidazole-4,7-diones as bioreductive anticancer agents," European Journal Medicinal Chemistry, vol. 43:1858-1864 (2008).
(Continued)

*Primary Examiner* — Paul V Ward
(74) *Attorney, Agent, or Firm* — Nelson Mullins Riley & Scarborough LLP; Jane E. Remillard, Esq.; Cynthia L. Kanik

(57) ABSTRACT

The present invention relates to a process for preparing a compound of formula [I], said process comprising the steps of: formula [II]+formula [III]→formula [I] (i) forming a reaction mixture comprising (a) a compound of formula [II], (b) a compound of formula [III] and (c) 1,2-propanediol or polyethylene glycol, or a mixture thereof, and optionally (d) a base; (ii) heating said reaction mixture to a temperature of at least about 150° C. to form a compound of formula [I]; (iii) isolating said compound of formula [I]; and (iv) optionally converting said compound of formula [I] into salt form; wherein: $R^1$ and $R^2$ are each independently H, alkyl or haloalkyl; $R^3$ and $R^4$ are each independently H, alkyl, haloalkyl or aryl; $R^5$ is alkyl, alkenyl, cycloalkyl or cycloalkyl-alkyl, each of which may be optionally substituted with one or more OH groups; $R^6$ is selected from cyclopropylamino, cyclopropylmethylamino, cyclobutylamino, cyclobutylmethylamino and formula (A) where one of X, Y and Z is N and the remainder are $CR^9$; $R^7$, $R^8$ and each $R^9$ are independently H, alkyl or haloalkyl, wherein at least one of $R^7$, $R^8$ and $R^9$ is other than H. Further aspects of the invention relate to a highly diastereoselective process for the preparation of compounds of formula [III], a process for preparing intermediates of formula [II], and other intermediates useful in the synthesis of compounds of formula [I], and to a process for preparing the crystalline tartrate salt and free base of compounds of formula [I].

(Continued)

-continued

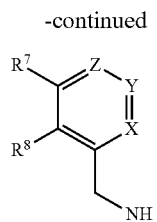

(A)

14 Claims, 2 Drawing Sheets

(30) Foreign Application Priority Data

Figure 1:
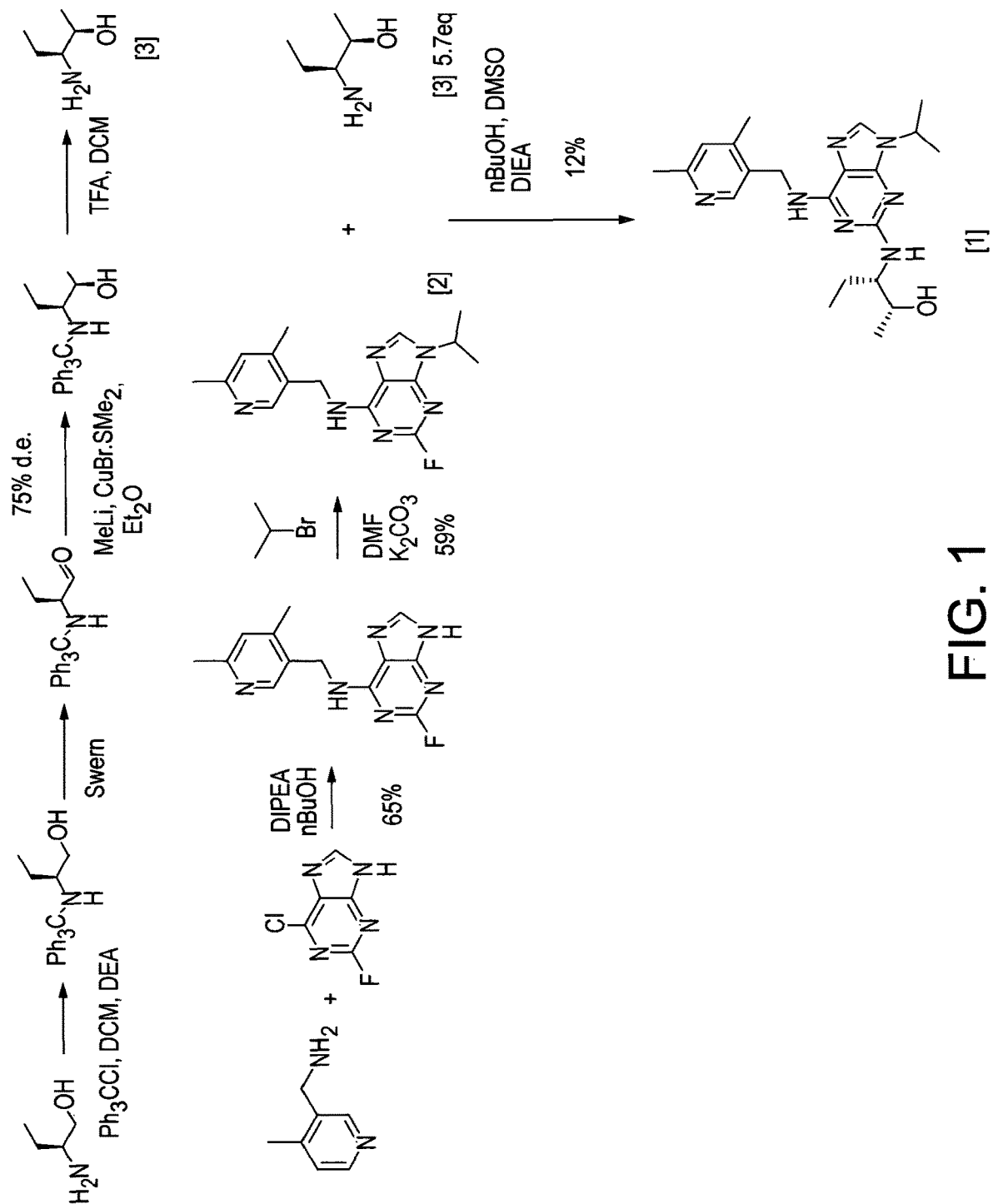

Jan. 27, 2017 (GB) .................................. 1701397.0
Jan. 27, 2017 (GB) .................................. 1701398.8

(56) References Cited

U.S. PATENT DOCUMENTS

| | | |
|---|---|---|
| 8,809,350 B2 | 8/2014 | Benigni et al. |
| 8,846,696 B2 | 9/2014 | Fischer et al. |
| 8,889,861 B2 | 11/2014 | Skead et al. |
| 9,573,951 B2 | 2/2017 | Skead et al. |
| 2005/0256142 A1 | 11/2005 | Fischer et al. |
| 2008/0125404 A1 | 5/2008 | Benigni et al. |
| 2009/0325983 A1 | 12/2009 | Fischer et al. |
| 2010/0009376 A1 | 1/2010 | Tomigahara et al. |
| 2012/0309723 A1 | 12/2012 | Benigni et al. |
| 2013/0072504 A1 | 3/2013 | Skead et al. |
| 2013/0116430 A1 | 5/2013 | Fujiwara et al. |
| 2015/0148354 A1 | 5/2015 | Skead et al. |

FOREIGN PATENT DOCUMENTS

| | | |
|---|---|---|
| WO | 2011089401 A1 | 7/2011 |
| WO | 2018/138500 A1 | 8/2018 |

OTHER PUBLICATIONS

Gharbaoui T et al., Derives N-alkyles en serie purine. Synthese par chimie radicalaire SRn1 et amenagements fonctionnels, Bull. Soc. Chim. Fr., vol. 131(5):561-574 (1994).

International Preliminary Report on Patentability, PCT/GB2018/050208, dated Jul. 30, 2019, 10 pages.

International Search Report and Written Opinion, PCT/GB2018/050208, dated Mar. 22, 2018, 12 pages.

Khlebnikov A I et al., N-Heterylethylenes VII. N-Alkenylation of Carbazole, Phenoxazine, and Phenothiazine by Carbonyl Compounds, Russian Journal of Organic Chemistry,vol. 29(9):1573-1576 (1993).

Lebedev A Y et al., "Palladium-Catalyzed Stereocontrolled Vinylation of Azoles and Phenothiazine," Organic Letters, vol. 4(4):623-626 (2002).

Lebedev A Y et al., "Palladium-Catalyzed Stereocontrolled Vinylation of Azoles and Phenothiazine," Supporting Information, 13 pages.

Shiraishi Y. et al., "A New Synthetic Method for Dipeptides Containing alpha, beta-Didehydroamino Acids Utilizing an alpha-Tosylglycine Residue," Bulletin for the Chemical Society of Japan, vol. 77 (Issue 12): 2219-2229 (2004).

Sonawane Y A et al., "Cyclin Dependent Kinase 9 Inhibitors for Cancer Therapy," Journal of Medicinal Chemistry, 2016, vol. 59:8667-8684 (2016).

Wattansin S. et al., "Methylenation of N-Acylheterocycles," Synthetic Communications,, vol. 19(15):2659-2664 (1989).

PROCESS FOR PREPARING PURINE DERIVATIVES

CROSS-REFERENCE TO RELATED APPLICATIONS

This application is a 35 U.S.C. 371 national stage filing of International Application No. PCT/GB2018/050208, filed on Jan. 25, 2018, which claims priority to United Kingdom Patent Application Serial No. 1701318.6, filed on Jan. 26, 2017; United Kingdom Patent Application Serial No. 1701319.4, filed on Jan. 26, 2017; United Kingdom Patent Application Serial No. 1701397.0, filed on Jan. 27, 2017; and United Kingdom Patent Application Serial No. 1701398.8, filed on Jan. 27, 2017. The contents of the aforementioned applications are hereby incorporated by reference in their entireties.

The present invention relates to a process for preparing purine derivatives, and intermediates and derivatives relating thereto.

BACKGROUND TO THE INVENTION

Purine derivatives exhibiting CDK inhibitory activity are disclosed in WO 2008/122767 (Cyclacel Limited; Cancer Research Technology Limited). By way of example, studies have demonstrated that compound [1], having the chemical name (2R,3S)-3-(6-((4,6-dimethylpyridin-3-ylmethyl-amino)-9-isopropyl-9H-purin-2-ylamino)pentan-2-ol, exhibits potent CDK inhibitory activity and thus has potential therapeutic applications in the treatment of proliferative disorders, immune-mediated and inflammatory disorders, autoimmune and autoimmune-mediated disorders, kidney disorders, cardiovascular disorders, ophthalmic disorders, neurodegenerative disorders, psychiatric disorders, viral disorders, metabolic disorders and respiratory disorders.

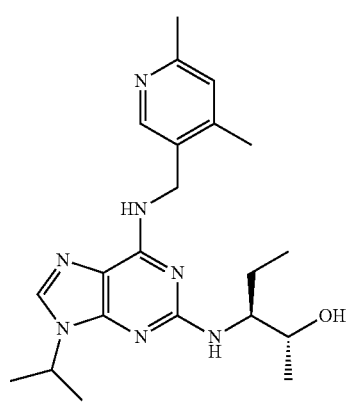

[1]

Advantageously, compound [1] displays surprisingly high potency in cellular toxicity studies in a range of different cell lines.

The synthetic preparation of compound [1] was first described in WO 2008/122767. The reaction scheme is shown in FIG. 1. The preparation involved synthesising fluoro-substituted purine derivative [2] and coupling with (2R,3S)-3-aminopentan-2-ol, [3]. The coupling reaction was carried out in "BuOH in the presence of DMSO and DIEA. The reaction required heating at a temperature of 140° C. for 72 hours and yielded only 12% of the desired product. Intermediate compound [3] was prepared via Swern oxidation of (S)-2-(trityl-amino)-butan-1-ol and subsequent reduction with MeLi and $CuBr.SMe_2$. The resulting intermediate was then treated with TFA to yield compound [3]. However, the MeLi/$CuBr.SMe_2$ reduction step led to poor stereoselectivity, yielding a product having only 75% diastereomeric excess (d.e.).

Figure 2:
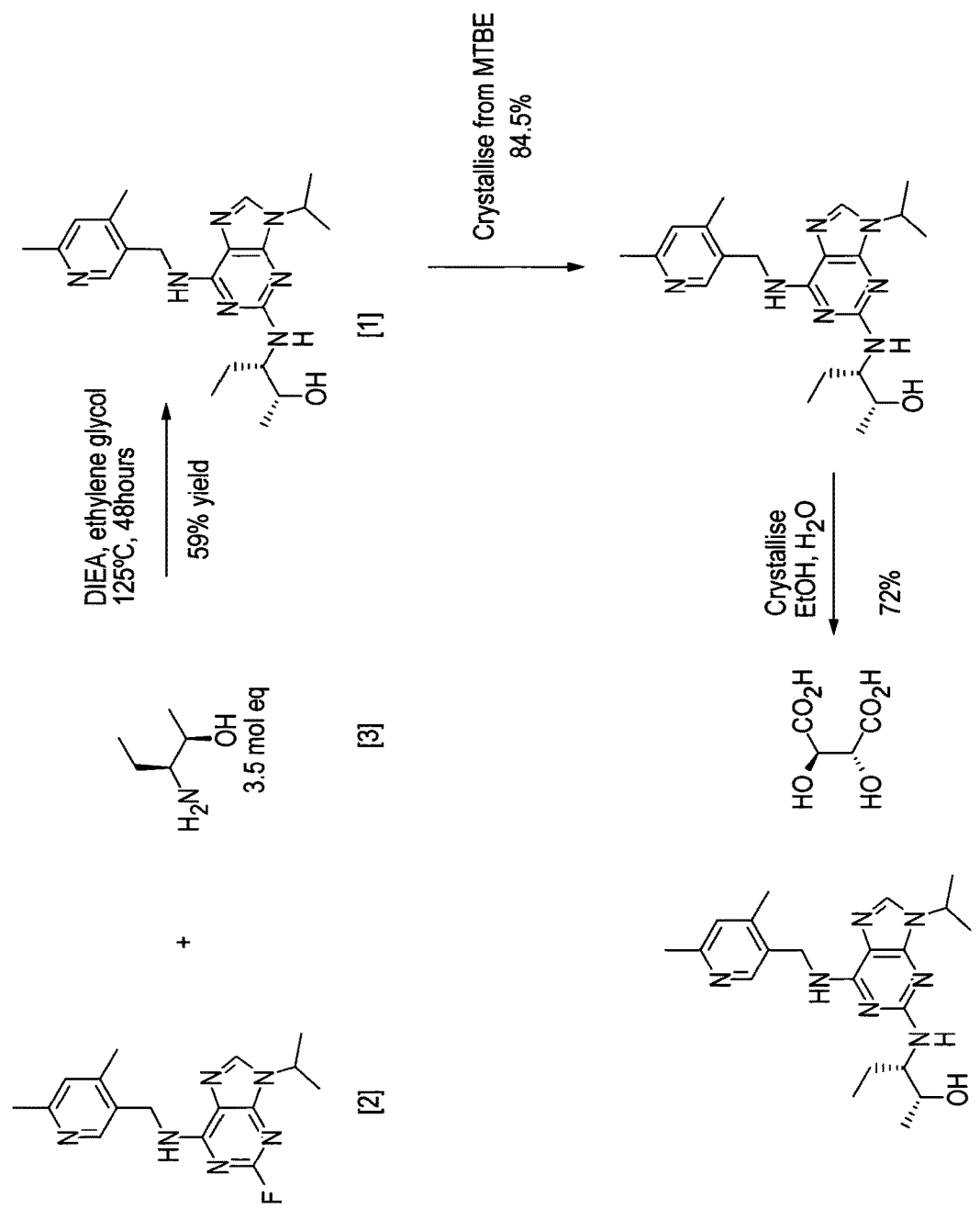

Alternative conditions for the coupling step were disclosed in WO 2011/089401 (Cyclacel Limited), as shown in FIG. 2. These alternative conditions involved reacting compound [2] with compound [3] in DIEA and ethylene glycol at a temperature of 125° C. for 48 hours. This gave rise to a marked improvement in the yield of crude compound [1] (59% cf 12% in WO 2008/122767), which was then crystallised from MTBE to give an overall yield of 49.4%. The crystalline free base material was subsequently converted to the crystalline L-tartrate salt (Form II; also referred to as Form E) in 72% yield by recrystallizing from an ethanol/water mixture.

The present invention seeks to provide an alternative synthetic preparation for CDK inhibitors such as compound [1], and intermediates and derivatives relating thereto. More specifically, but not exclusively, the present invention seeks to provide a synthetic route which is suitable for scale up and/or which gives rise to one or more of improved yields, improved purity, improved stereoselectivity, improved ease of preparation, faster reaction times, reduced amounts of/fewer side products, and/or requiring reduced amounts of reagents.

STATEMENT OF INVENTION

A first aspect of the invention relates to a process for preparing a compound of formula [I],

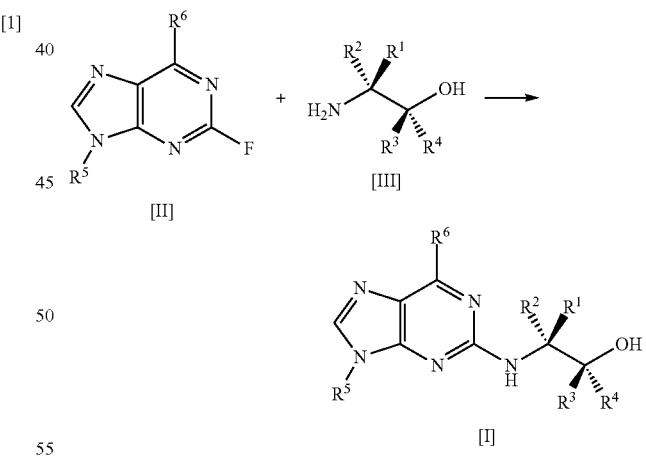

wherein:

$R^1$ and $R^2$ are each independently H, alkyl or haloalkyl;

$R^3$ and $R^4$ are each independently H, alkyl, haloalkyl or aryl;

$R^5$ is alkyl, alkenyl, cycloalkyl or cycloalkyl-alkyl, each of which may be optionally substituted with one or more OH groups;

$R^6$ is selected from cyclopropylamino, cyclopropylmethylamino, cyclobutylamino, cyclobutylmethylamino and

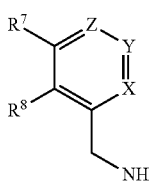

where one of X, Y and Z is N and the remainder are $CR^9$;

$R^7$, $R^8$ and each $R^9$ are independently H, alkyl or haloalkyl, wherein at least one of $R^7$, $R^8$ and each $R^9$ is other than H;

said process comprising the steps of:
(i) forming a reaction mixture comprising (a) a compound of formula [II], (b) a compound of formula [III] and (c) 1,2-propanediol or polyethylene glycol, or a mixture thereof;
(ii) heating said reaction mixture to a temperature of at least about 150° C. to form a compound of formula [I];
(iii) isolating said compound of formula [I]; and
(iv) optionally converting said compound of formula [I] into salt form.

Advantageously, the applicant has shown that the above-described coupling conditions lead to a marked improvement in the yield. For example, for compound [1] (structure shown below), using 1,2-propanediol in step (i), the overall yield of crystalline free base is ca. 79%=compared to 59% in WO 2011/089401.

A second aspect of the invention relates to a process for preparing the crystalline L-tartrate salt of compound [1], said process comprising the steps of refluxing a solution of compound [1] in ethanol and adding dropwise thereto a solution of L-tartaric acid in a mixture of water and ethanol, wherein the ratio of ethanol:water in the final mixture after addition of the L-tartaric acid solution is at least about 15:1

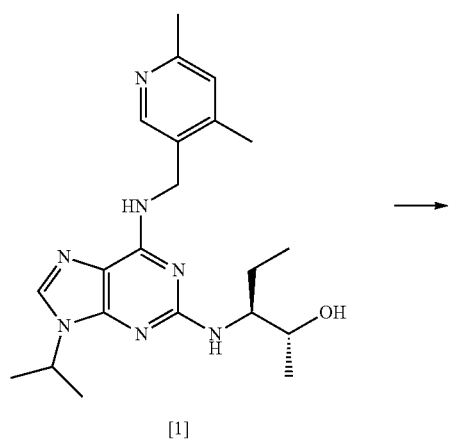

[1]

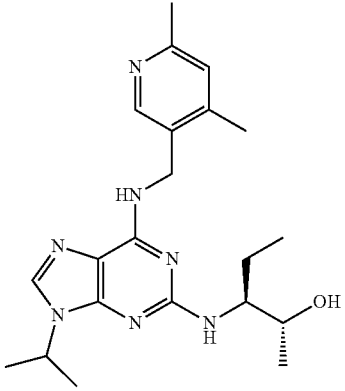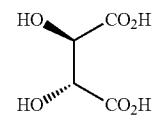

[1]-L-tartrate salt

Advantageously, the applicant has shown that increasing the proportion of ethanol relative to water in the crystallisation step leads to a marked improvement in the yield of the crystalline tartrate salt of compound [1] relative to the yields disclosed in the art (ca. 87% compared with 72% in Example 5.5 of WO 2011/089401).

A third aspect of the invention relates to a process for preparing a compound of formula [IV] or [III]:

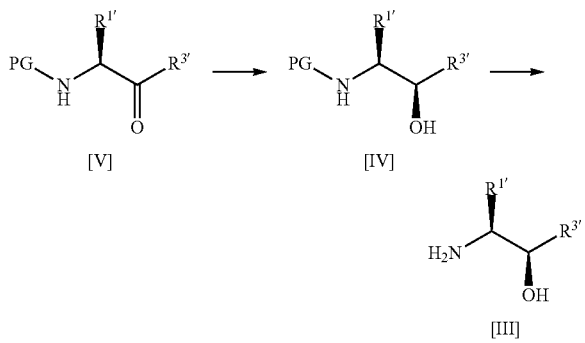

wherein:
$R^{1'}$ is alkyl or haloalkyl;
$R^{3'}$ is alkyl, haloalkyl or aryl; and
PG is a protecting group;

said process comprising the steps of:
(a') treating a compound of formula [V] with (S)-2-Me-CBS-oxazoborolidine and borane-N,N-diethylaniline complex in a solvent comprising THF to form a compound of formula [IV]; and
(b') optionally removing the protecting group PG from said compound of formula [IV] to give a compound of formula [III].

Advantageously, the applicant has shown that the above conditions lead to a highly diastereoselective reduction, imparting a very high diastereomeric excess (ca. 99%) in the resulting intermediate. This diastereomeric excess far exceeds the levels observed for preparation of such intermediates according to prior art methods; see for example, WO 2003/002565 (Cyclacel Limited) or WO 2008/122767 (Cyclacel Limited; Cancer Research Technology Limited).

A fourth aspect of the invention relates to a process for preparing a compound of formula [II] by the steps of:

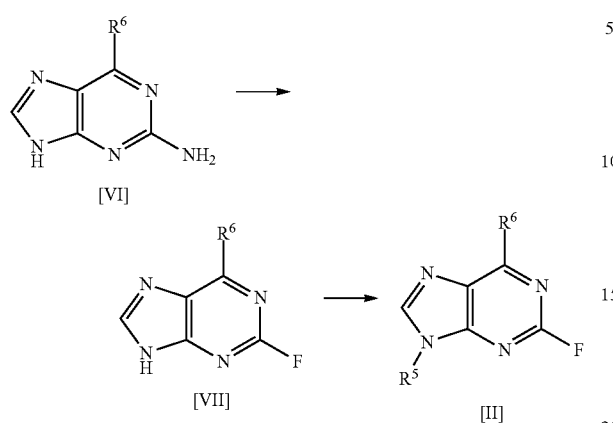

(i) treating a compound of formula [VI] with HF, pyridine and ᵗBuONO to form a compound of formula [VII]; and
(ii) treating said compound of formula [VII] with R⁵Br in DMSO and K₂CO₃ to form a compound of formula [II]; wherein R⁵ and R⁶ are as defined above for the first aspect of the invention.

A fifth aspect of the invention relates to a process for preparing compound [2] by the steps of:

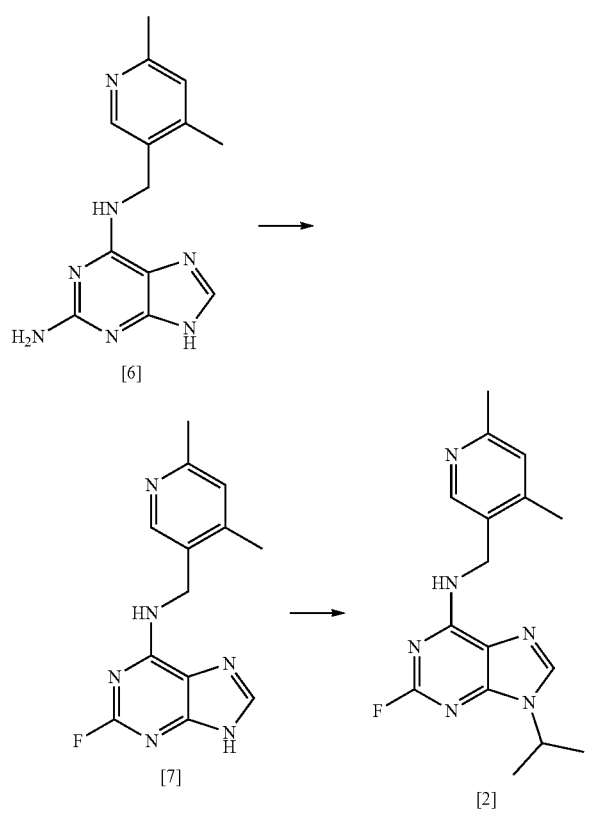

(i) treating compound [6] with HF, pyridine and ᵗBuONO to form compound [7]; and
(ii) treating said compound [7] with isopropyl bromide in DMSO and K₂CO₃ to form compound [2].

A sixth aspect of the invention relates to a compound [6]:

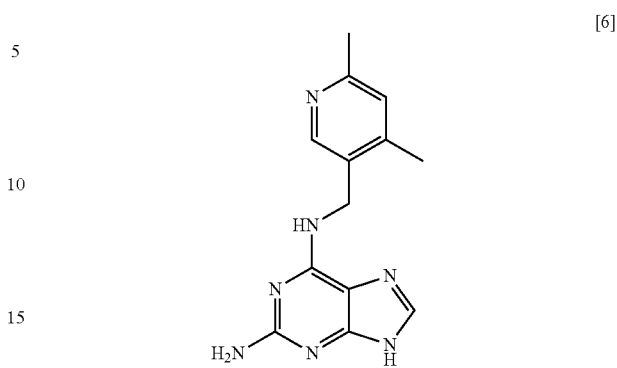

A seventh aspect of the invention relates to compound [6] for use as an intermediate in the preparation of compound [1].

An eighth aspect of the invention relates to a process for preparing compound [1], said process comprising the steps of:
(i) preparing compound [2] from a compound of formula [6] as described above; and
(ii) reacting compound [2] with a compound [3] as described above to form compound [1].

DETAILED DESCRIPTION

Process for Preparing Compounds of Formula [I]

The present invention provides a new procedure for the synthesis of compounds of general formula [I], and in particular, the specific compound [1]. By way of illustration, the applicant has shown that the use of high purity intermediate [2] is critical in order to obtain free base compound [1] in sufficient purity to attain the target specification of compound [1]-L-tartrate salt. Crystallisation of the free base of compound [1] is achieved following the inclusion of a seeding event in the procedure. The tartrate salt formation/crystallisation has also been successfully modified over the prior art conditions to improve the overall yield of the final stage giving compound [1]-L-tartrate salt.

As mentioned, a first aspect of the invention relates to a process for preparing a compound of formula [I], said process comprising the steps of:
(i) forming a reaction mixture comprising (a) a compound of formula [II], (b) a compound of formula [III] and (c) 1,2-propanediol or polyethylene glycol, or a mixture thereof;
(ii) heating said reaction mixture to a temperature of at least about 150° C. to form a compound of formula [I];
(iii) isolating said compound of formula [I]; and
(iv) optionally converting said compound of formula [I] into salt form.

In one preferred embodiment, the reaction mixture in step (i) optionally further comprises a base, more preferably a tertiary aliphatic amine base. More preferably, the base is selected from N,N-diisopropylethylamine (DIEA), tri-$^N$propylamine, and tri-$^N$butylamine. More preferably still, the base is N,N-diisopropylethylamine (DIEA).

Preferably, where the reaction mixture comprises a base, it is present in an amount of at least about 2 molar equivalents relative to the compound of formula [II], more preferably, about 2 to about 6 molar equivalents relative to the compound of formula [II], more preferably, about 2 to about 4 molar equivalents relative to the compound of formula [II]. In one preferred embodiment the base is present in an amount of about 2 molar equivalents relative to the compound of formula [II]. In another preferred embodiment the base is present in an amount of about 3 molar equivalents relative to the compound of formula [II]. In another preferred embodiment the base is present in an amount of about 4 molar equivalents relative to the compound of formula [II]. In another embodiment, the base is absent.

In one preferred embodiment, step (i) comprises forming a reaction mixture comprising (a) a compound of formula [II], (b) a compound of formula [III], (c) 1,2-propanediol, and (d) a base, preferably DIEA.

In another preferred embodiment, step (i) comprises forming a reaction mixture comprising (a) a compound of formula [II], (b) a compound of formula [III], and (c) 1,2-propanediol.

In another preferred embodiment, step (i) comprises forming a reaction mixture comprising (a) a compound of formula [II], (b) a compound of formula [III], (c) polyethylene glycol, and (d) a base, preferably DIEA.

In another preferred embodiment, step (i) comprises forming a reaction mixture comprising (a) a compound of formula [II], (b) a compound of formula [III], and (c) polyethylene glycol.

Preferably, the polyethylene glycol is a liquid polyethylene glycol. The skilled person would be familiar with different forms of polyethylene glycol. More preferably, the polyethylene glycol is PEG-200 or PEG-400, more preferably PEG-200. PEG-200 and PEG-400 and similar such liquid polyethylene glycols can be obtained from commercial sources (e.g. Sigma Aldrich; Dow, under the tradename CARBOWAX™).

In one preferred embodiment, one of $R^1$ and $R^2$ is H and the other is alkyl.

More preferably, one of $R^1$ and $R^2$ is H and the other is methyl, ethyl or isopropyl.

Even more preferably, $R^1$ is ethyl and $R^2$ is H.

In one preferred embodiment, $R^3$ and $R^4$ are each independently H, alkyl, haloalkyl or aryl, and wherein at least one of $R^3$ and $R^4$ is other than H.

In one preferred embodiment, one of $R^3$ and $R^4$ is H and $R^4$ the other is alkyl or haloalkyl.

In one preferred embodiment, $R^3$ is H and $R^4$ is alkyl or haloalkyl.

In one preferred embodiment, $R^3$ is H and $R^4$ is methyl.

In one preferred embodiment, $R^6$ is:

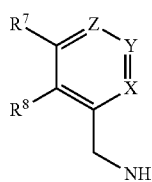

In one preferred embodiment, Y is N. Preferably for this embodiment:
X is CH, Z is C-Me and $R^7$ is H and $R^8$ is Me; or
X is CH, Z is C-Me and $R^7$ and $R^8$ are both H; or
X is CH, Z is C—$CF_3$ and $R^7$ and $R^8$ are both H.

In another preferred embodiment, X is N. Preferably for this embodiment:
Y is C-Me, Z is CH and $R^7$ and $R^8$ are both H; or
Y and Z are CH, $R^7$ is H and $R^8$ is Me.

In another preferred embodiment Z is N. Preferably, for this embodiment, X is CH, Y is C-Me, $R^7$ is Me and $R^8$ is H.

In another preferred embodiment, $R^6$ is cyclopropylamino, cyclopropylmethylamino, cyclobutylamino or cyclobutylmethylamino.

In one preferred embodiment, $R^5$ is isopropyl or isopropenyl, more preferably, isopropyl.

In one highly preferred embodiment, the compound of formula [I] is selected from the following:

---

2R,3S-3-(6-((4,6-Dimethylpyridin-3-ylmethylamino)-9-isopropyl-9H-purin-2-ylamino)pentan-2-ol 2R,3S-3-(6-Cyclopropylamino)-9-isopropyl-9H-purin-2-ylamino)pentan-2-ol 2R,3S-3-(6-(Cyclopropylmethylamino)-9-isopropyl-9H-purine-2-ylamino)pentan-2-ol 2R,3S-3-(6-(Cyclobutylamino)-9-isopropyl-9H-purin-2-ylamino)pentan-2-ol 2R,3S-3-(9-Isopropyl-6-(2,6-dimethylpyridine-4-ylmethylamino)-9H-purin-2-ylamino)pentan-2-ol 2R,3S-3-(9-Isopropyl-6-((6-(trifluoromethyl)pyridine-3-yl)methylamino)-9H-purin-2ylamino)pentan-2-ol 2R,3S-3-(9-Isopropyl-6-((6-methylpyridin-2-yl)methylamino)-9H-purin-2-ylamino)pentan-2-ol 2R,3S-3-(9-Isopropyl-6-((3-methylpyridin-2-yl)methylamino)-9H-purin-2-ylamino)pentan-2-ol 1,1,1-Trifluoro-3-(9-isopropyl-6-((6-(trifluoromethyl)pyridin-3-yl)methylamino)-9H-2-ylamino)pentan-2-ol

---

In one preferred embodiment:
the compound of general formula [I] is compound [1];
the compound of general formula [II] is compound [2]; and
the compound of general formula [III] is compound [3];
i.e. the invention relates to a process which comprises the steps of:

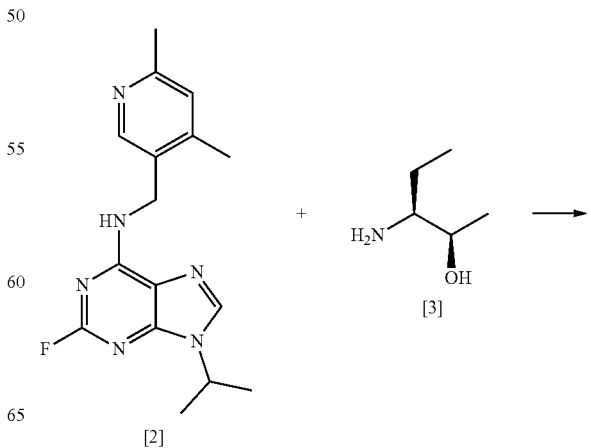

-continued

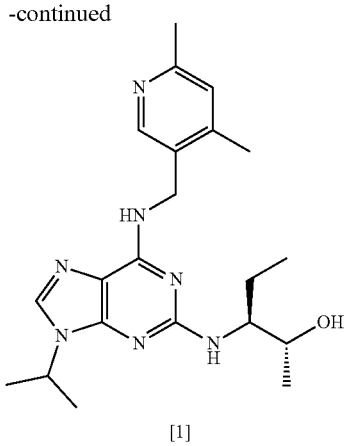

[1]

(i) forming a reaction mixture comprising (a) a compound of formula [2], (b) a compound of formula [3] and (c) 1,2-propanediol or polyethylene glycol, or a mixture thereof;
(ii) heating said reaction mixture to a temperature of at least about 150° C. to form a compound of formula [1];
(iii) isolating said compound of formula [1]; and
(iv) optionally converting said compound of formula [1] into salt form.

In one preferred embodiment, the reaction mixture in step (i) optionally further comprises a base, preferably, a tertiary aliphatic amine base. More preferably, the base is selected from N,N-diisopropylethylamine (DIEA), tri-$^N$propylamine, and tri-$^N$butylamine. More preferably still, the base is N,N-diisopropylethylamine (DIEA).

Preferably, where the reaction mixture comprises a base, it is present in an amount of at least about 2 molar equivalents relative to the compound of formula [2], more preferably, about 2 to about 6 molar equivalents relative to the compound of formula [2], more preferably, about 2 to about 4 molar equivalents relative to the compound of formula [2]. In one preferred embodiment the base is present in an amount of about 2 molar equivalents relative to the compound of formula [2]. In another preferred embodiment the base is present in an amount of about 3 molar equivalents relative to the compound of formula [2]. In another preferred embodiment the base is present in an amount of about 4 molar equivalents relative to the compound of formula [2].

In one preferred embodiment, step (i) comprises forming a reaction mixture comprising (a) a compound of formula [2], (b) a compound of formula [3], (c) 1,2-propanediol, and (d) a base, preferably DIEA.

In another preferred embodiment, step (i) comprises forming a reaction mixture comprising (a) a compound of formula [2], (b) a compound of formula [3], and (c) 1,2-propanediol.

In another preferred embodiment, step (i) comprises forming a reaction mixture comprising (a) a compound of formula [2], (b) a compound of formula [3], (c) polyethylene glycol, and (d) a base, preferably DIEA. Preferably, the polyethylene glycol is PEG-200 or PEG-400, more preferably, PEG-200.

In another preferred embodiment, step (i) comprises forming a reaction mixture comprising (a) a compound of formula [2], (b) a compound of formula [3], and (c) polyethylene glycol. Preferably, the polyethylene glycol is PEG-200 or PEG-400, more preferably, PEG-200.

In one preferred embodiment, the reaction mixture is heated to a temperature of from about 150° C. to about 180° C., more preferably from about 150° C. to about 170° C., more preferably from about 150° C. to about 160° C., even more preferably from about 150° C. to about 155° C.

Even more preferably, the reaction mixture is heated to a temperature of about 150° C.

In another preferred embodiment, the reaction mixture is heated for a period of at least 48 hours. In a more preferred embodiment, the reaction mixture is heated for a period of at least 24 hours. In another preferred embodiment, the reaction mixture is heated for a period of at least 12 hours. In another preferred embodiment, the reaction mixture is heated for a period of at least 72 hours. In one highly preferred embodiment, the reaction mixture is heated for a period of about 24 hours. In another highly preferred embodiment, the reaction mixture is heated for a period of about 48 hours. In another highly preferred embodiment, the reaction mixture is heated for a period of about 72 hours.

In another preferred embodiment, the reaction mixture is heated for a period of from about 24 to about 96 hours, more preferably, from about 24 to about 72 hours, or from about 24 to about 48 hours. In another preferred embodiment, the reaction mixture is heated for a period of from about 48 to about 96 hours, more preferably, from about 48 to about 72 hours.

In one preferred embodiment, the 1,2-propanediol or polyethylene glycol is present in an amount of at least about 2 volume equivalents relative to a compound of formula [II] (or formula [2]), more preferably, about 2 to about 20 volume equivalents relative to a compound of formula [II] (or formula [2]), more preferably, about 2 to about 10 volume equivalents relative to a compound of formula [I] (or formula [2]). In one preferred embodiment the base is present in an amount of about 5 to about 10 volume equivalents relative to a compound of formula [II] (or formula [2]). In another preferred embodiment the base is present in an amount of about 5 volume equivalents relative to a compound of formula [II] (or formula [2]). In one preferred embodiment the base is present in an amount of about 9 equivalents relative to a compound of formula [II] (or formula [2]).

Advantageously, the present process allows for a reduced molar equivalent of the compound of formula [III] to be used relative to compound [II], compared to methods described in the art (see WO 2008/122767, which requires 5.7 equivalents of compound [3] in the preparation of compound [1], and WO 2011/089401, which requires 3.5 equivalents). This is beneficial in terms of minimising the use of reagents and ease of purification, as well as for economic reasons in scale up.

Thus, in one preferred embodiment, the reaction mixture comprises from about 2 to about 3 mole equivalents of compound [III] relative to compound [II]. More preferably, the reaction mixture comprises from about 2 to about 2.5 or about 2 to about 2.2 mole equivalents of compound [III] relative to compound [II]. Even more preferably, the reaction mixture comprises about 2 mole equivalents of compound [III] relative to compound [II].

In one particularly preferred embodiment, in the context of preparing compound [1], the reaction mixture comprises from about 2 to about 3 mole equivalents of compound [3] relative to compound [2]. More preferably, the reaction mixture comprises from about 2 to about 2.5 or about 2 to about 2.2 mole equivalents of compound [3] relative to compound [2]. Even more preferably, the reaction mixture comprises about 2 mole equivalents of compound [3] relative to compound [2].

In one highly preferred embodiment, the process comprises forming a reaction mixture comprising (a) a compound of formula [II], (b) a compound of formula [III] (2 equivalents), (c) 1,2-propanediol (5 vol), and (d) DIEA (4 equivalents) and heating said reaction mixture to a temperature of about 150° C. for a period of about 72 hours. In an alternative preferred embodiment, the DIEA is omitted.

In one highly preferred embodiment, the process comprises forming a reaction mixture comprising (a) a compound of formula [II], (b) a compound of formula [III] (2 equivalents), (c) polyethylene glycol, preferably, PEG-400 or PEG-200 (5 vol), and (d) DIEA (4 equivalents) and heating said reaction mixture to a temperature of about 150° C. for a period of about 72 hours. In an alternative preferred embodiment, the DIEA is omitted.

In one highly preferred embodiment, the process comprises forming a reaction mixture comprising (a) a compound of formula [2], (b) a compound of formula [3] (2 equivalents), (c) 1,2-propanediol (5 vol), and (d) DIEA (4 equivalents) and heating said reaction mixture to a temperature of about 150° C. for a period of about 72 hours. In an alternative preferred embodiment, the DIEA is omitted.

In one highly preferred embodiment, the process comprises forming a reaction mixture comprising (a) a compound of formula [2], (b) a compound of formula [3] (2 equivalents), (c) polyethylene glycol, preferably, PEG-400 or PEG-200 (5 vol), and (d) DIEA (4 equivalents) and heating said reaction mixture to a temperature of about 150° C. for a period of about 72 hours. In an alternative preferred embodiment, the DIEA is omitted.

In one preferred embodiment, step (iii) comprises extracting the reaction mixture from step (ii) into water and ethyl acetate, separating the ethyl acetate phase and drying with a drying agent, filtering and concentrating the filtrate. Suitable drying agents (for example, magnesium sulfate) will be familiar to the skilled person in the art.

In one preferred embodiment, step (iii) further comprises the step of azeotroping the concentrated filtrate with tertiary butyl methyl ether (TBME).

In one preferred embodiment, in the context of preparing compound [1], step (iii) further comprises the step of crystallizing compound [1] from tertiary butyl methyl ether (TBME). Preferably, this step comprises heating at reflux and seeding with a crystal of compound [1] prepared in accordance with the procedures of WO 2011/089401, the contents of which are hereby incorporated by reference (see, in particular, Example 1). Preferably, the seeded mixture is cooled to a temperature of from about 50 to about 55° C.

Preferably, the mixture is stirred at this temperature for about 30 minutes and then allowed to cool to room temperature.

Salt Formation

In one preferred embodiment, the process comprises the step of converting said compound of formula [1] into the L-tartrate salt, more preferably the L-tartrate salt in crystalline form. Even more preferably, the L-tartrate salt is crystalline form II (corresponding to Form E as described in WO 2011/089401) and can be prepared by the methods described therein (see Example 5.5).

Thus, in one preferred embodiment, the process comprises a crystallisation step which involves refluxing the product isolated in step (iii) in ethanol and adding dropwise thereto a solution of L-tartaric acid in a mixture of water and ethanol.

In one particularly preferred embodiment, the ratio of ethanol:water in the final mixture after addition of the L-tartaric acid solution is at least 15:1, more preferably, at least 20:1, more preferably at least 25:1, even more preferably still, at least 30:1. Advantageously, increasing the proportion of ethanol relative to water in the crystallisation step leads to a marked improvement in the yield of the crystalline tartrate salt of compound [1] relative to the yields disclosed in the art (ca. 87% compared with 72% in Example 5.5 of WO 2011/089401).

In one particularly preferred embodiment, the ratio of ethanol:water in the final mixture after addition of the L-tartaric acid solution is about 37.5:1.

In one preferred embodiment, the process comprises maintaining the temperature at 75 to 78° C. during the addition of the solution of L-tartaric acid.

In one preferred embodiment, the crystallisation step further comprises polish filtering the mixture, warming the filtrate to a temperature of about 60 to about 65° C. and seeding with crystalline [1]-L-tartrate form II. Crystalline [1]-L-tartrate form II (also known as Form E) can be prepared in accordance with the teachings of WO 2011/089401, the contents of which are incorporated herein by reference (Cyclacel Limited).

In one preferred embodiment, the seeded filtrate is stirred at a temperature of about 60 to about 65° C. for at least 1 hour.

In one preferred embodiment, the process further comprises the step of cooling the mixture to a temperature of about 15 to about 20° C. and stirring at that temperature for at least 1 hour to induce crystallisation of compound [1]-L-tartrate. Preferably, the cooling rate is about 5 to about 10° C./hour, more preferably about 10° C./hour.

In one preferred embodiment, the compound [1]-L-tartrate is filtered, washed with ethanol and dried in vacuo.

As mentioned above, in the context of the coupling reaction, the applicant has shown that the use of a high purity intermediate of formula [II] is critical in order to obtain the free base compound of formula [I] in sufficient purity to attain the target specification of compound [I]-L-tartrate salt.

In one preferred embodiment, the compound of formula [II] (e.g. compound [2]) is passed through a silica pad, slurried in diethyl ether, filtered and dried prior to step (i).

In one preferred embodiment, the compound of formula [II] (e.g. compound [2]) has a purity of at least 97%, more preferably, at least 97.5% even more preferably, at least 98% by HPLC.

The applicant has additionally shown that the use of a compound of formula [III] with high disastereromic purity (i.e. a high d.e.) is also important in order to obtain good yields in the coupling reaction with compounds of formula [II]. In this respect, the present invention provides an alternative process for preparing compounds of formula [III], which leads to excellent disastereroselectivity, for example, d.e. values greater than or equal to 99%. Using compounds of general formula [III] with high disastereromic purity in the coupling step enables compounds of formula [I] to be prepared in high yield without the need for chromatographic separation from its stereoisomer. Instead, the crude product can simply be isolated and purified by crystallisation from MTBE, which has obvious advantages in terms of efficiency of scale up.

In one preferred embodiment, the compound of formula [III] (e.g. compound [3]) has a diastereomeric excess of at least 85%, more preferably, at least 90%, even more preferably, at least 95%.

In one highly preferred embodiment, the compound of formula [III] (e.g. compound [3]) has a diastereomeric excess of at least 96, 97, 98 or 99%.

In one preferred embodiment, the compound of formula [III] is prepared by the steps of:

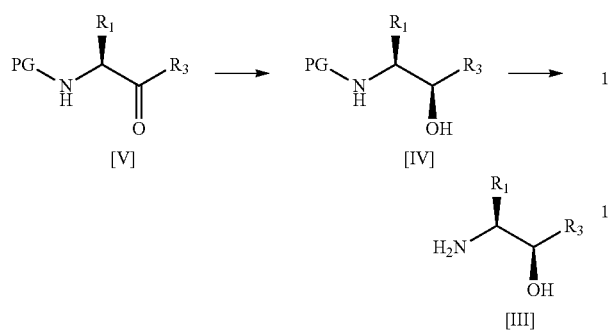

wherein:
R¹ is alkyl or haloalkyl;
R³ is alkyl, haloalkyl or aryl; and
PG is a protecting group;
said process comprising:
(a) treating a compound of formula [V] with (S)-2-Me-CBS-oxazoborolidine and borane-N,N-diethylaniline complex in a solvent comprising THF to form a compound of formula [IV]; and
(b) removing the protecting group PG from said compound [IV] to give a compound of formula [III].

In one preferred embodiment, step (b) comprises treating said compound [IV] with gaseous HCl in methanol, concentrating in vacuo, dissolving in ethyl acetate and then sparging with $NH_3$.

In one highly preferred embodiment, the compound of formula [III] is compound [3], which is prepared by the steps of:

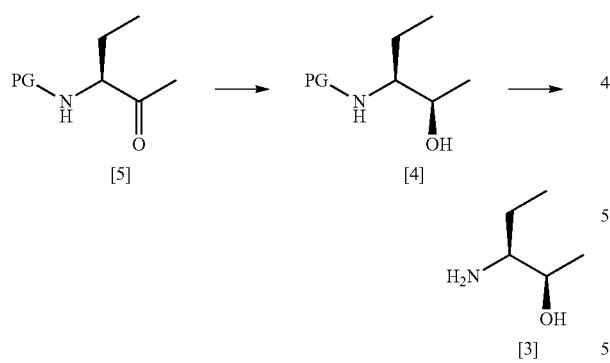

(a) treating a compound [5] with (S)-2-Me-CBS-oxazoborolidine and borane-N,N-diethylaniline complex in a solvent comprising THF to form a compound [4]; and
(b) removing the protecting group PG from said compound [4] to give compound [3].

Suitable amine protecting groups will be familiar to the skilled person; see for example, Protective Groups in Organic Synthesis by Theodora W. Greene and Peter G. M. Wuts. Preferably, the protecting group PG is a t-butyloxycarbonyl (Boc) group.

Process for Preparing Compounds of Formula [II]

Another aspect of the invention relates to a process for preparing compounds of formula [II] by the steps of:

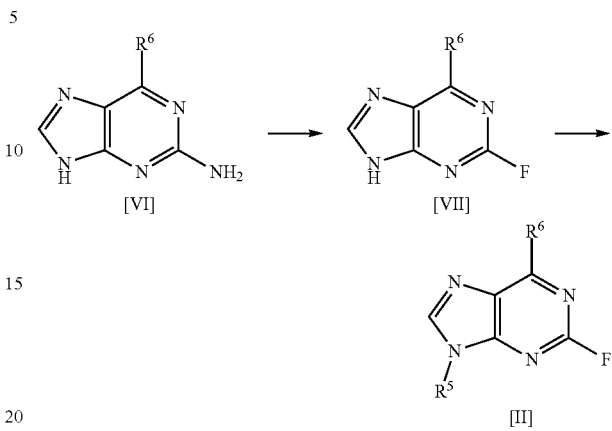

(i) treating a compound of formula [VI] with HF, pyridine and $^t$BuONO to form a compound of formula [VII]; and
(ii) treating said compound of formula [VII] with $R^5$Br in DMSO and $K_2CO_3$ to form a compound of formula [II];
where $R^5$ and $R^6$ are as defined above.

In a highly preferred embodiment, the invention relates to a process for preparing compound [2] by the steps of:

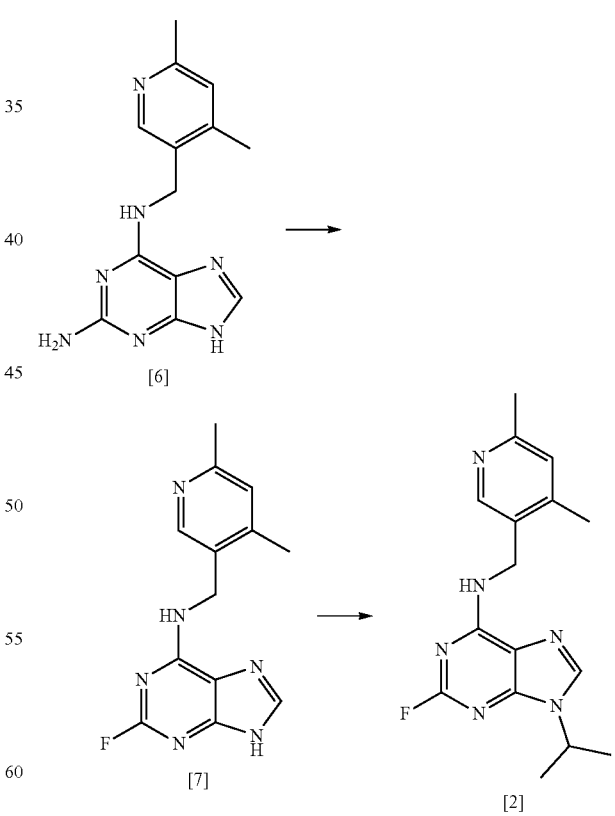

(i) treating compound [6] with HF, pyridine and $^t$BuONO to form compound [7]; and
(ii) treating said compound [7] with isopropyl bromide in DMSO and $K_2CO_3$ to form compound [2].

Another aspect of the invention relates to compound [6].

Another aspect of the invention relates to compound [6] for use as an intermediate in the preparation of compound [1].

Another aspect of the invention relates to a process for preparing compound [1], said process comprising the steps of:

(i) preparing compound [2] from a compound of formula [6] as described above; and
(ii) reacting compound [2] with a compound [3] as described above to form compound [1].

Further details of the synthetic process according to the invention are described below, with reference to the reaction scheme set out in Scheme 1:

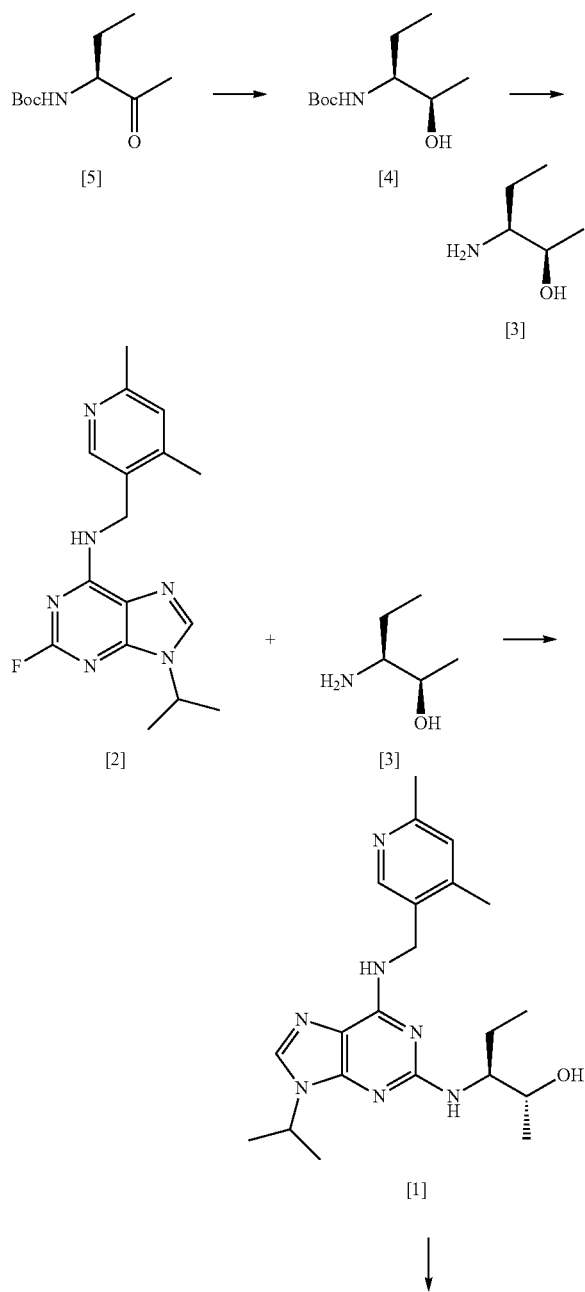

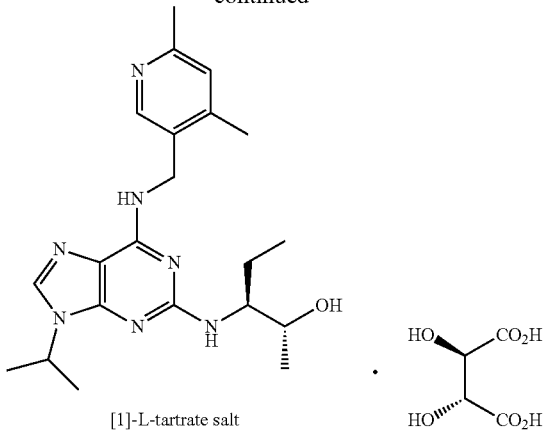

[1]-L-tartrate salt

The reaction was successfully carried out on a 115 g scale to give the desired product compound [4] in 85% yield (99.2 g) as a white solid.

Boc deprotection of compound [4] proceeded cleanly to the desired HCl salt of compound [3]. Free base formation was then achieved by sparging ammonia through a suspension of the HCl salt in ethyl acetate to give compound [3] as a light yellow oil in 95% overall yield (48.7 g). $^1$H NMR analysis indicated the material isolated was suitable for use in the coupling step.

The applicant has found that the purity of compound [2] also has a significant effect on the final coupling reaction. To assess the effect of higher purity [2] on the final coupling reaction profile, 55 g of compound [2] (96.80% purity by HPLC) was passed through a silica pad eluting with 15% MeOH in DCM. The resulting product was then slurried in diethyl ether, filtered and dried to give 49.3 g of compound [2] with a purity of 98.46% by HPLC.

The final coupling reaction was carried out in 1,2-propanediol (5 vol) with 2 equivalents of compound [3] at 150° C.

A use-test of the purified compound [2] and the bulk batch of compound [3] was carried out on a 1 g scale (2 eq compound [3] in 5 vol 1,2-propanediol at 150° C.). After 18 hours, HPLC indicated 94.13% compound [1], 1.74% compound [2] and 1.66% propanediol adduct. Although the reaction was not complete, the above result confirmed the use of high purity compound [2] to be critical in order to achieve >90% conversion to product (cf. 87% conversion to compound [1] when compound [2] of 96.80% purity was used).

A 10 g scale final coupling reaction was carried out, giving 93.11% conversion to product (1.4% 1,2-propanediol adduct), and providing crude free base compound [1] with a purity of 95.54% by HPLC (1.3% 1,2-propanediol adduct) after workup. $^1$H NMR confirmed removal of 1,2-propanediol was successful in the workup. The crude product (12.2 g) was recrystallised from TBME (2 volumes TBME). Crystallisation occurred when a seed of crystalline free base compound [1] was added (seed prepared in accordance with the teachings of WO 2011/089401; Cyclacel Limited; Form A, Example 1). The resulting solid was filtered and dried to give free base compound [1] in 81% overall yield (from compound [2] input, target 79%) with a purity of 97.84% by HPLC, (0.95% 1,2-propanediol adduct, target purity >97%). This material was carried through to the tartrate salt formation.

A large scale final coupling reaction was then performed on a 36.2 g scale. The reaction proceeded as expected giving 95.01% conversion to product (0.29% 1,2-propanediol adduct). Workup provided crude free base compound [1] as a white foamy solid (46.9 g) with a purity of 95.22% by HPLC (0.20% 1,2-propanediol adduct, 1.74% RRT 0.98). A seeded recrystallisation from TBME (using seed crystal of Form A as described above) gave crystalline free base compound [1] in an overall yield of 79% and with a purity of 97.32% (0.14% 1,2-propanediol adduct, 1.10% RRT 0.98).

Compound [1] (87.6% purity) was then converted to the corresponding crystalline L-tartrate salt. A trial salt formation was carried out on a 5 g scale using material from the large scale coupling reaction. A ratio of 37.5:1 ethanol:water was used. Following tartaric acid addition, a seed of form II was added at 60-65° C. which did not dissolve. The reaction was stirred at 60-65° C. for 1 hour (during which crystallisation initiated) then cooled to 15-20° C. over 1 hour. After stirring at 15-20° C., the resulting solids were isolated and dried. This yielded compound [1]-L-tartrate salt in a yield of 83% (from free base, 65% overall yield from compound [2] input) with a purity of 98.57% (0.15% 1,2-propanediol adduct, 0.37% RRT 0.98). $^1$H NMR confirmed a 1:1 salt and XRPD confirmed form II.

A large scale salt formation was then carried out on a 29.9 g scale using the above conditions to confirm the process. Isolation yielded compound [1]-L-tartrate salt in a yield of 87% (from free base, 69% overall yield from compound [2] input) with a purity of 98.80% (0.37% 1,2-propanediol adduct, 0.02% RRT 0.98). $^1$H NMR confirmed a 1:1 salt and XRPD confirmed form II.

The applicant has thus demonstrated that the use of higher purity compound [2] in the final coupling reaction is critical to obtain ~95% conversion to compound [1]. The free base compound [1] can then be converted to the corresponding crystalline L-tartrate form in good yield.

Process for Preparing the Crystalline L-Tartrate Salt of Compound [1]

Another aspect of the invention relates to a process for preparing the crystalline L-tartrate salt of compound [1]. The process comprising the steps of refluxing a solution of compound [1] in ethanol and adding dropwise thereto a solution of L-tartaric acid in a mixture of water and ethanol, wherein the ratio of ethanol to water is at least 15:1

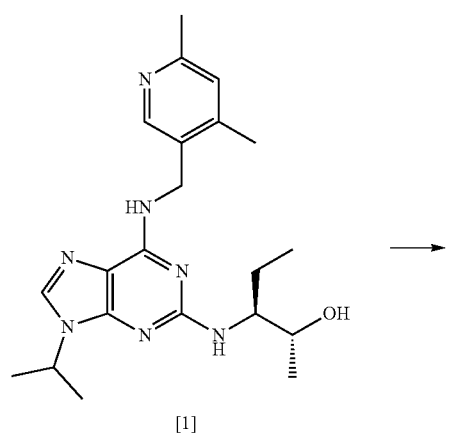

[1]

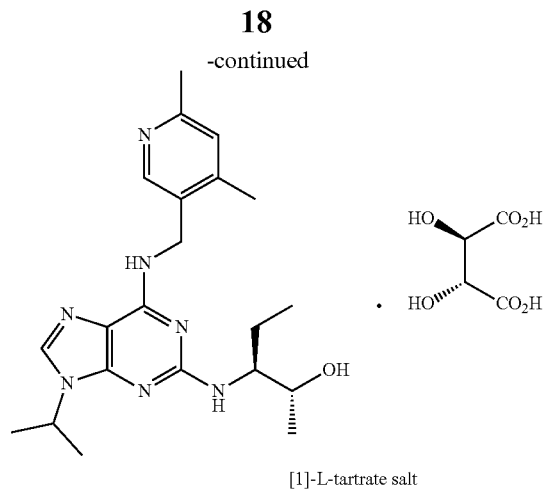

[1]-L-tartrate salt

In one preferred embodiment, the ratio of ethanol:water in the final mixture after addition of the L-tartaric acid solution is at least 20:1, more preferably, at least 25:1, even more preferably at least 30:1, even more preferably, at least 35:1.

In one preferred embodiment, the ratio of ethanol:water in the final mixture after addition of the L-tartaric acid solution is about 37.5:1.

Preferably, the temperature is maintained at 75 to 78° C. during the addition of the solution of L-tartaric acid.

In one preferred embodiment, the process comprises the step of polish filtering the mixture, warming the filtrate to a temperature of about 60 to about 65° C. and seeding with crystalline [1]-L-tartrate form II.

In one preferred embodiment, the process comprises stirring the seeded filtrate at a temperature of about 60 to about 65° C. for at least 1 hour.

In one preferred embodiment, the process further comprises the step of cooling the mixture to a temperature of about 15 to about 20° C. and stirring at that temperature for at least 1 hour to induce crystallisation of compound [1]-L-tartrate.

Preferably, the cooling rate is about 5 to about 10° C./hour, more preferably, about 10° C./hour.

In one preferred embodiment, the compound [1]-L-tartrate is filtered, washed with ethanol and dried in vacuo.

Diastereoselective Process for Preparing Compounds of Formula [III]

Another aspect of the invention relates to a disastereoselective process for preparing compounds of formula [III] with high diastereomeric excess.

Thus, in one aspect, the invention relates to a process for preparing a compound of formula [IV] or [III]:

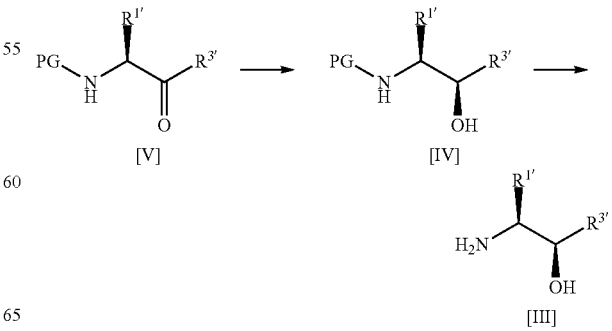

wherein:
R[1'] is alkyl or haloalkyl;
R[3'] is alkyl, haloalkyl or aryl; and
PG is a protecting group;
said process comprising the steps of:
(a') treating a compound of formula [V] with (S)-2-Me-CBS-oxazoborolidine and borane-N,N-diethylaniline complex in a solvent comprising THF to form a compound of formula [IV]; and
(b') optionally removing the protecting group PG from said compound of formula [IV] to give a compound of formula [III].

In one highly preferred embodiment, the process comprises the steps of:

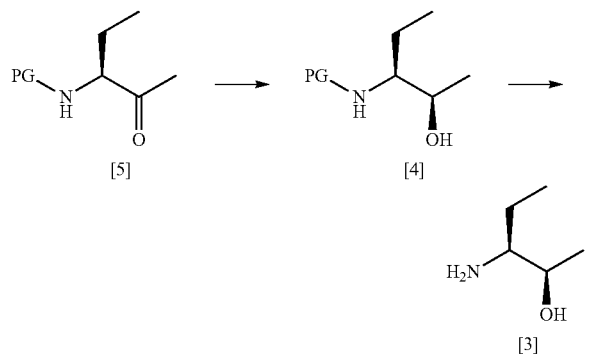

(a') treating a compound [5] with (S)-2-Me-CBS-oxazoborolidine and borane-N,N-diethylaniline complex in a solvent comprising THF to form a compound [4]; and
(b') optionally removing the protecting group PG from said compound [4] to give a compound [3].

Advantageously, the above conditions lead to a highly diastereoselective reduction, imparting a very high diastereomeric excess (ca. 99%) in the resulting intermediate. This diastereomeric excess far exceeds the levels observed for preparation of such intermediates according to prior art methods; see for example, WO 2003/002565 (Cyclacel Limited; d.e. of 80%) or WO 2008/122767 (Cyclacel Limited; Cancer Research Technology Limited; d.e. of 75%).

In one preferred embodiment, the (S)-2-Me-CBS-oxazoborolidine is a solution in toluene.

In one preferred embodiment, step (a') comprises (i) adding the borane-N,N-diethylaniline complex dropwise to a mixture of (S)-2-Me-CBS-oxazoborolidine in THF; and (ii) adding the compound of formula [V] (e.g. compound [5]) in THF dropwise to the mixture formed in step (i).

Preferably, the mixture formed in step (ii) is stirred at room temperature for at least 12 hours.

In one preferred embodiment, step (a') further comprises crystallizing the compound of formula [IV] (e.g. compound [4]) from heptane.

In one preferred embodiment, step (b') comprises treating said compound of formula [IV] (e.g. compound [4]) with gaseous HCl in methanol, concentrating in vacuo, dissolving in ethyl acetate and then sparging with $NH_3$.

The present invention is further described with reference to the following figures, wherein:
FIG. 1 shows the reaction scheme for preparing compound [1] as disclosed in WO 2008/122767.
FIG. 2 shows the reaction scheme for preparing compound [1]-L-tartrate as disclosed in WO 2011/089401.

The present invention is further described with reference to the following non-limiting Examples.

EXAMPLES

Abbreviations

THF tetrahydrofuran
EtOAc ethyl acetate
PMA phosphomolybdic acid
MeOH methanol
DCM dichloromethane
TBME tertiary butyl methyl ether
DCM dichloromethane
DIEA N,N-diisopropylethylamine
$^1$H NMR: $^1$H NMR spectra were collected using a JEOL ECX 400 MHz spectrometer equipped with an auto-sampler. The samples were dissolved in $D_6$-DMSO for analysis and the spectrum was acquired at ambient temperature using a standard proton experiment acquiring 16 scans using Delta NMR Processing and Control Software version 4.3. The data were then processed using ACD labs 1D NMR processor version 12.0.

DSC: DSC data were collected on a PerkinElmer Pyris 6000 DSC equipped with a 45 position sample holder. The instrument was verified for energy and temperature calibration using certified indium. A predefined amount of the sample, 0.5-3.0 mg, was placed in a pin holed aluminium pan and heated at 20° C.·$min^{-1}$ from 30 to 350° C., or varied as experimentation dictated. A purge of dry nitrogen at 20 ml·$min^{-1}$ was maintained over the sample. The instrument control, data acquisition and analysis were performed with Pyris Software v 11.1.1 Revision H.

XRPD: X-Ray Powder Diffraction patterns were collected on a PANalytical diffractometer using Cu Kα radiation (45 kV, 40 mA), θ-θ goniometer, focusing mirror, divergence slit (½"), soller slits at both incident and divergent beam (4 mm) and a PIXcel detector. The software used for data collection was X'Pert Data Collector, version 2.2f and the data was presented using X'Pert Data Viewer, version 1.2d.

XRPD patterns were acquired under ambient conditions via a transmission foil sample stage (polyimide-Kapton, 12.7 μm thickness film) under ambient conditions using a PANalytical X'Pert PRO. The data collection range was 2.994-35028 with a continuous scan speed of 0.202004°$s^{-1}$.

HPLC: Method A
Sample Solution Preparation:
Accurately weigh 50 mg of sample into a 100 ml volumetric flask. Add 50 ml of Methanol to the flask, dissolve via sonication if necessary, dilute to volume with Purified Water and mix the resulting solution thoroughly.
Column: 150×4.6 mm Luna C18 (2), 5 μm particle size, (ex-Phenomenex; #OOF-4252-EO)
Mobile Phase: A—0.01 M Ammonium Acetate Buffer (pH 8.0)
B—Acetonitrile
Flow Rate: 1.0 ml·$min^{-1}$
Injection Volume: 5 μl
Detection: UV@ 254 nm
Column Temp: 30° C.
Post Run: 5 minutes
HPLC Method B
Sample Solution Preparation:
Accurately weigh 50 mg of sample into a 100 ml volumetric flask. Add 50 ml of Methanol to the flask, dissolve via sonication if necessary, dilute to volume with Purified Water and mix the resulting solution thoroughly.

Column: 150×4.6 mm XBridge Phenyl, 3.5 μm particle size, (ex-Waters; #186003335)
Mobile Phase: A—Purified Water: Trifluoroacetic acid (100: 0.1)
  B—Acetonitrile: Trifluoroacetic acid (100:0.1)
Flow Rate: 1.0 ml·min$^{-1}$
Injection Volume: 5 μl
Detection: UV@ 268 nm
Column Temp: 30° C.
Post Run: 5 minutes
  Chiral HPLC
Column: 250×4.6 mm Chiralpak AD-H, 5 μm particle size, (ex-Daicel Chemical Industries, Ltd; #DAIC 19325)
Mobile Phase: Ethanol:Hexane (50:50)
Flow Rate: 1.0 ml·min$^{-1}$
Injection Volume: 20 μl
Detection: UV@ 268 nm
Column Temp: 40° C.
Run Time: 20 minutes
  HRGC:
  Sample Solution Preparation
Accurately weigh 50 mg of sample into a 10 ml volumetric flask. Dissolve in 5 ml of dichloromethane, using sonication if required, dilute to volume with dichoromethane and mix the resulting solution thoroughly.
Column: DB-1 30 m×0.32 mm; 1.0 μm film thickness (ex-J&W Scientific #123-1033)
Oven Program: 40° C. (Hold 5 mins) then 10° C.·min$^{-1}$ to 300° C.
  (Hold 10 mins)
Injector Temperature: 200° C., split
Column Temperature: 250° C., F.I.D.
Head Pressure: 12 psi, constant pressure
Carrier Gas: Nitrogen
Spilt Ratio: 50:1
Injection Volume: 2 μl
Liner: SGE Focusliner with glass wool insert
  Enantiomeric Excess by HRGC:
  Standard Solution Preparation
Accurately weigh 10 mg of each enantiomer [(2R,3S); (2S,3R); (2R,3R); (2S,3S)] into a suitable container. Dissolve in about 1 ml of HPLC grade dichloromethane, sonicating if necessary. Add 500 μl of trifluoroacetic anhydride and 500 μl of trifluoroacetic acid and allow to derivatise for 15-30 minutes at room temperature. Inject this solution.
  Sample Solution Preparation
Accurately weigh, in duplicate, 10 mg of sample into a suitable container. Dissolve in about 1 ml of HPLC grade dichloromethane, sonicating if necessary. Add 500 μl of trifluoroacetic anhydride and 500 μl of trifluoroacetic acid and allow to derivatise for 15-30 minutes at room temperature. Inject this solution.
Column: Gamma-TA Cyclodextrin 30 m×0.32 mm; 0.125 μm film (ex-Astec; Cat no. 73033)
Oven Program: 80° C. (Hold 10 mins) then 2° C.·min$^{-1}$ to 90° C.
  (Hold 20 mins) then 10° C.·min$^{-1}$ to 80° C.
Injector Temperature: 200° C., split
Column Temperature: 250° C., F.I.D.
Head Pressure: 20 psi, constant pressure
Carrier Gas: Nitrogen
Spilt Ratio: 50:1
Injection Volume: 1 μl
Liner: SGE Focusliner with glass wool insert $$\% \text{ enantiomeric excess} = \frac{\text{Peak area of } [(2R, 3S) - (2S, 3R)]}{\text{Peak area of } [(2R, 3S) + (2S, 3R)]} \times 100\%$$

$$\% \text{ diastereomeric excess} = \frac{\text{Peak area of } [(2R, 3S) - (2S, 3S)]}{\text{Peak area of } [(2R, 3S) + (2S, 3S)]} \times 100\%$$

(2R,3S)-3-aminopentan-2-ol Synthesis

Preparation of Compound [4]

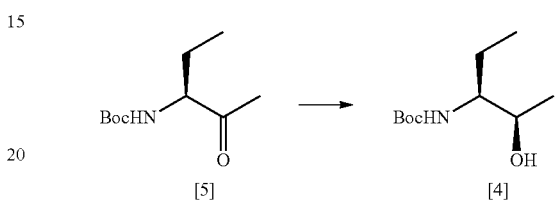

(S)-2-Methyl-CBS-oxaborolidine (1M solution in toluene, 59.6 mL, 0.06 mol) was diluted with THF (171 mL) in a dry, nitrogen purged vessel. Borane N,N-diethylaniline complex (102 mL, 0.57 mol) was added dropwise at room temperature and the solution was allowed to stir for 15 minutes. Compound [5] (115.0 g, 0.57 mol) was dissolved in THF (345 mL) and added dropwise over 4.5 h. After the addition was complete the reaction was allowed to stir overnight at room temperature under a nitrogen atmosphere. Thin layer chromatography (20% EtOAc in heptane, visualised by PMA) indicated the complete consumption of starting material. The reaction was carefully quenched via dropwise addition of methanol (174 mL) over 1 h. The temperature was maintained at <20° C. throughout the quench. The solution was concentrated in vacuo before additional methanol (174 mL) was added. The solution was concentrated under reduced pressure to afford a white waxy solid. The crude product was recrystallised from heptane (202 mL). The recrystallised product was filtered and rinsed with heptane (2×156 mL) to yield a white solid. This was dried in a vacuum oven at 40° C. overnight to give compound [4] as a white solid (99.2 g, 85%). Analysis was by HRGC and chiral HRGC as described above.

Deprotection of Compound [4]

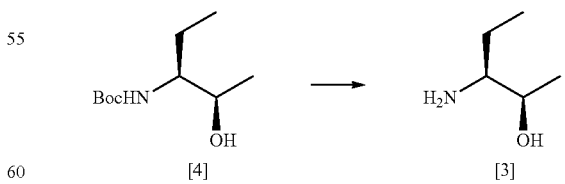

MeOH (645 mL) was gassed with HCl for 1 hour at <20° C. in a 20 L flask under N$_2$. The solution was 3.85M by titration. The flask was cooled to <15° C. Compound [4] (101.1 g, 0.50 mol) was charged portion-wise at <15° C. The solution was stirred overnight. The reaction was complete by TLC (5% MeOH/DCM, visualised with PMA). The solution was concentrated in vacuo at 35-40° C. The oil was azeotroped with EtOAc (4×75 mL) and triturated to give a white solid. The solid was taken up in EtOAc (588 mL). The reaction mixture was cooled to 0-5° C. and sparged with NH₃ (g) for 1 hour at 0-5° C. under N₂. At the end of the addition the pH was 8. The mixture was filtered and the filter cake was washed with EtOAc (147 mL). The filtrate was concentrated in vacuo at 35-40° C. to give the desired product [3] as a light yellow oil (50.7 g). $^1$H NMR confirmed the identity of the product and indicated ~4% residual EtOAc to be present giving an active yield of 48.7 g, 95%.

Preparation of Compound [7]

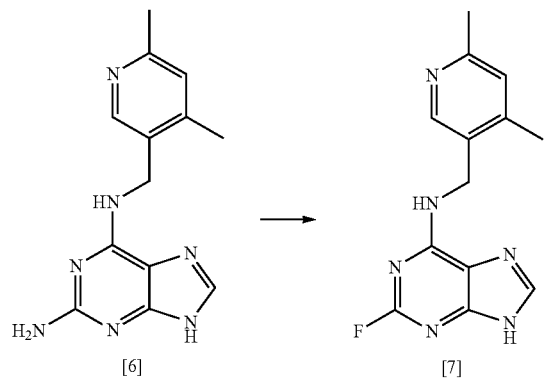 [SMILES: Cc1cc(C)c(CNc2nc(N)nc3[nH]cnc23)cn1 ; Cc1cc(C)c(CNc2nc(F)nc3[nH]cnc23)cn1]

60% HF/pyridine (2982.3. g) was charged to a 6 L PTFE vessel and cooled to between −35 and −30° C. Compound [6] (322.2 g, 1 mol eq) was charged to the vessel maintaining the batch temperature between −35 and −30° C. The vessel contents were allowed to warm to between −15 and −10° C., then tert-butyl nitrite (160 ml, 1 mol eq) was added dropwise maintaining the temperature between −15 and −5° C. The batch was allowed to warm to room temperature (between 15 and 20° C.) and stirred for 17 hours. The batch was sampled for completion by HPLC which indicated the presence of 11.3% compound [6]. Additional tert-butyl nitrite (48 ml, 0.3 mol eq) was added and stirred for 3 hours, a completion check showed 2.3% compound [6] remaining. Additional tert-butyl nitrite was added (48 ml, 0.3 mol eq) and stirred overnight. A final completion indicated 0.7% compound [6] remained. The reaction mixture was quenched into sat.aq. K₂CO₃ (12000 ml), additional sat.aq. K₂CO₃ (3500 ml) was added to adjust to pH 8, the batch was stirred for 90 minutes then filtered. The filter was washed with purified water (3200 ml). The solid was returned to the quench vessel and slurried in purified water (3200 ml) for 34 minutes and filtered. The filter was washed with purified water (3200 ml). The solid was returned to the quench vessel and slurried in purified water (3200 ml) for 34 minutes and filtered. The filter was washed with purified water (3200 ml) and TBME (3×1600 ml). The solid was dried at 45° C. under vacuum. Yield=222.5 g (68.3%); purity 94.9% by HPLC (Method A).

Preparation of Compound [2]

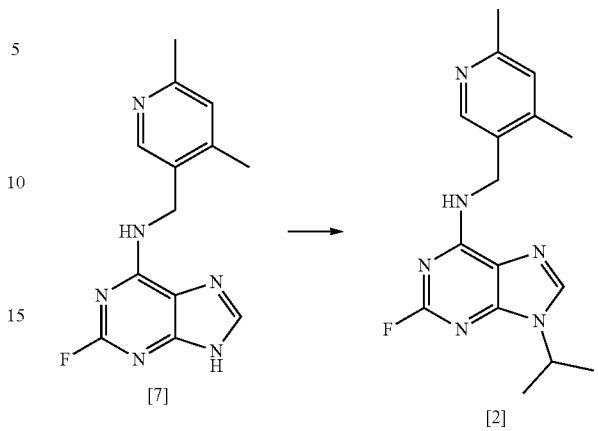

The reaction was carried out in one batch which was split into four portions for the workup and then purified in two portions achieving an overall yield of 2261.6 g (79% vs target 85%).

Under N₂ was charged DMSO (25000 ml), compound [7] (2479.9 g 1 mol eq) and potassium carbonate (2504.7 g 2 mol eq). 2-bromopropane (8520 ml 10 mol eq) was added maintaining the batch temperature between 15 and 25° C. The reaction mixture was heated to 60° C. and stirred for 35 minutes maintaining the temperature between 58 and 62° C. The reaction mixture was sampled for completion analysis. HPLC (Method A) indicated the reaction was complete, (0.14% compound [7] remaining). The reaction mixture was cooled to between 18 and 25° C. The batch was split into 4 approximately equal portions. Each portion was returned to the vessel with purified water (11200 ml) and ethyl acetate (11200 ml), stirred for 10 minutes and the layers separated.

Reaction Work-Up

The aqueous layer was charged to the vessel and extracted with ethyl acetate (3×6200 ml). The combined organic layers were charged to the vessel and washed with purified water (6×9300 ml). The organic layer was dried over magnesium sulphate (1014.1 g) and filtered. The filter cake was washed with ethyl acetate (3×2500 ml). The batch solution was sampled for HPLC analysis which indicated a crude purity of 94.1%.

Purification

The dried organic layers were combined into two portions. Each portion was distilled from the 50 L vessel until minimum stir and then transferred to a 2 L rotary evaporator to complete the concentration. The crude compound [2] (1480.5 g) was dissolved in 15% MeOH/EtOAc (3000 ml) in a carboy. Silica (2961.3 g) was charged to the carboy and the contents were agitated over 15 minutes. Further 15% MeOH/EtOAc (2000 ml) was charged to the carboy to help slurry the silica. A plate filter was set up and packed with silica (4441.5 g) in 15% MeOH/EtOAc. The crude compound [2]/silica slurry was transferred to the filter plate and packed. The silica pad was then washed with 15% MeOH/EtOAc (88800 ml) collected in 5 fractions, 15% MeOH/EtOAc (44360 ml) collected in 2 fractions and 15% MeOH/EtOAc (44360 ml) collected in 2 fractions. Fractions containing compound [2] were polish filtered and concentrated. The resulting solid was azeotroped with EtOAc (3×3000 ml) and dried in a vacuum oven overnight at 30° C. Yield=1090.3 g; purity 96.9% by HPLC (Method A).

The corresponding alkenyl analogue of compound [2] can be prepared as follows. A suspension of compound [7] (1.0 g) and phosphorus pentoxide (1.04 g, 2 eq) in toluene (40 ml), collidine (0.9 g, 2 eq) and acetone (2.1 g, 10 eq) was heated at reflux with stirring overnight. The reaction was cooled to room temperature and filtered. The filter cake was stirred with sat. aq. NaHCO$_3$ (30 ml) and toluene (30 ml) for 5 minutes and then refiltered. The phases were separated and the aqueous was extracted with toluene (30 ml). The combined organics were dried (sodium sulfate) filtered and concentrated in vacuo. The product was purified by chromatography (silica 65 g) eluent=EtOAc→10% MeOH in EtOAc) to afford 190 mg of product ~90% pure by $^1$H NMR and a further 0.1 g of less pure material. The less pure product was recolumned (silica 51 g, eluent=4% MeOH in DCM) to give additional product (70 mg). Total yield 260 mg (22.7%). The alkenyl analogue of [2] can be reacted with compound [3] (3-10 eq) in PEG200 and DIPEA by heating overnight at 120-130° C. The product can be purified by column chromatography using 4% MeOH in DCM as eluent to give the product in >95 purity by $^1$H NMR.

Purification of Compound [2]

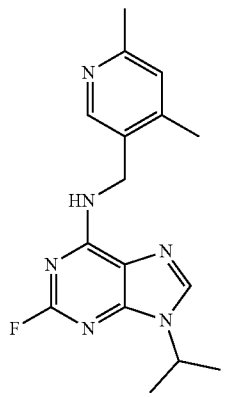

[2]

In order to assess the effect of higher purity compound [2] on the final coupling reaction profile, 55 g of compound [2] (96.80% purity by HPLC) was passed through a silica pad eluting with 15% MeOH in DCM. The resulting product was then slurried in diethyl ether, filtered and dried to give 49.3 g of compound [2] with a purity of 98.46% by HPLC (Method A).

Preparation of Compound [1] Using 1,2-Propanediol in Step (i)

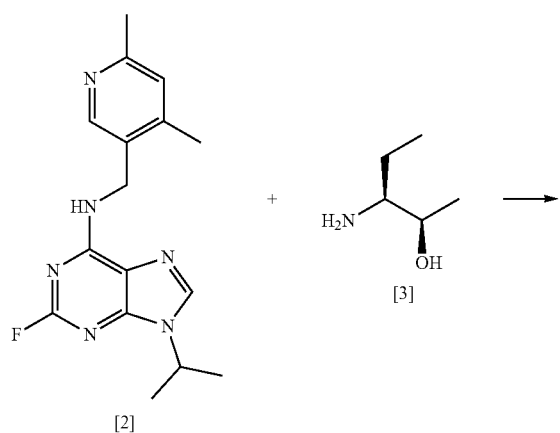

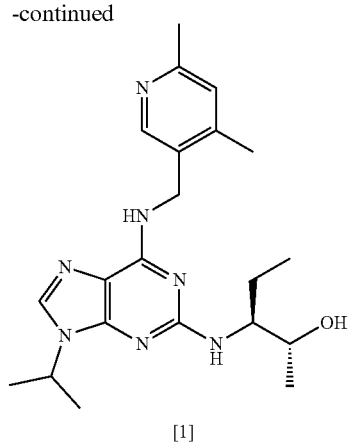

[1]

A solution of compound [2] (36.2 g, 115.15 mmol) and compound [3] (24.7 g, 23.8 g active, 230.71 mmol) in 1,2-propanediol (181 mL) was heated at 150° C. overnight. Analysis by HPLC (Method B) indicated 0.29% propanediol adduct, 95.01% compound [1] and 0.57% compound [4]. Alternatively, PEG-200 can be used instead of 1,2-propanediol. Optionally the reaction mixture further comprises DIEA (2 mole equivalents). After cooling to 15-20° C., water (250 mL) and ethyl acetate (120 mL) were charged to the vessel and the batch was stirred for 10 minutes. The layers were separated and the aqueous layer was extracted with ethyl acetate (4×100 mL). The combined organic layers were washed with 2.5 w/w % brine (3×160 mL) then water (3×160 mL). The organic layer was dried over MgSO$_4$ and filtered. The filtrate was concentrated then azeotroped with TBME (2×250 mL) to isolate the crude compound [1] free base (46.9 g). HPLC analysis indicated a purity of 95.22% (Method B).

The crude material (46.9 g) was taken up in TBME (94 mL) and heated at reflux. A seed of crystalline compound [1] (0.009 g; prepared in accordance with the teachings of WO 2011/089401; Form A; Cyclacel Limited) was added and the resulting hazy solution was cooled to 50-55° C. and stirred for 30 minutes. The seed crystal was prepared in accordance with Example 1 of WO 2011/089401 (Cyclacel Limited). The reaction mixture was then allowed to cool to room temperature overnight. The resulting solid was filtered, washed with TBME (3×47 mL) and pulled dry. The off-white solid was dried at 40° C. under vacuum to give crystalline compound [1] free base (36.0 g, 79%; Form A). XRPD and DSC characterisation was in accordance with Form A, WO 2011/089401; see Table 1 for reference XRPD peaks). Optionally, the secondary hydroxyl group of compound [1] can be oxidised by treating with an oxidising agent, such as pyridium chlorochromate (0.2 equiv) and periodic acid (2.5 equiv) in MeCN as solvent, e.g. stirring at room temperature for 21 h, and then recharging with further pyridinium chlorochromate and periodic acid as necessary in order to drive the reaction to completion (followed by purification using column chromatography).

Preparation of Compound [1] Using PEG-200 and DIEA in Step (i)

A small scale reaction reaction was run to compare HPLC reaction profiles of a reaction using PEG-200 in direct comparison to 1,2-propanediol. Thus, under N$_2$ was charged compound [2] (1.0 g, 3.181 mmol) and the reaction solvent (9.0 mL, 9 volumes). The mixture was then stirred for 5 minutes before the addition of the DIEA (2.2 mL, 4 eq) and compound [3] (0.66 g, 6.362 mol), the reactions were then heated to temperature (150° C.). The reaction profile are shown after 72 h are shown in the table below.

| Solvent | Compound [1] HPLC area % | Compound [2] HPLC area % | Largest Single Impurity HPLC area % |
|---|---|---|---|
| 1,2-Propanediol | 89.55% | 0.16% | Single impurities ≤3.25% |
| PEG-200 | 87.66% | 2.33% | Single impurities ≤3.60% |

Synthesis of Compound [1]-L-Tartrate Salt

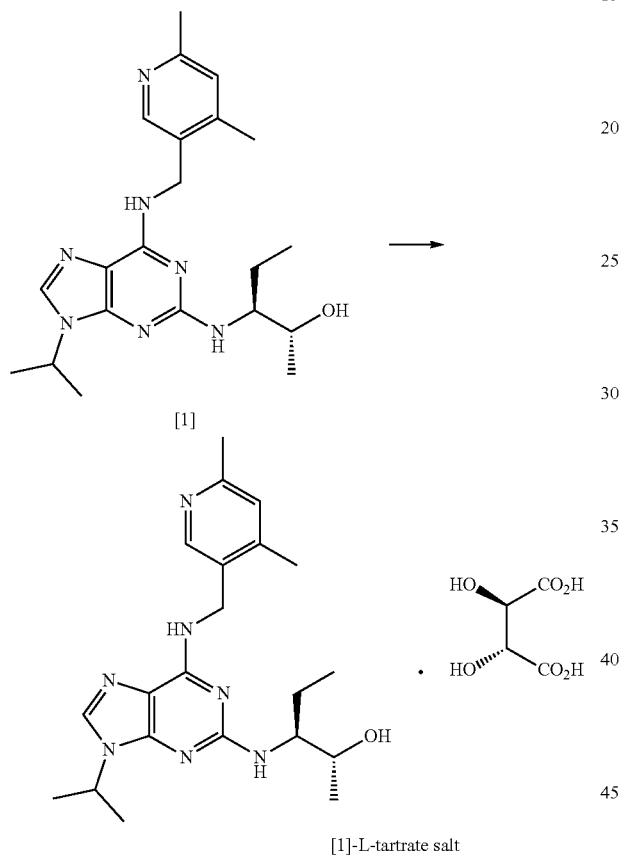

Crystalline compound [1] free base (29.9 g, 75.22 mmol) was dissolved in ethanol (420 mL) and the resulting solution heated at reflux. A solution of L-tartaric acid (11.29 g, 75.22 mmol) in water (12 mL)/ethanol (30 mL) was added dropwise maintaining the batch temperature at 75-78° C. The solution was polish filtered (cooled to 57° C. during filtration with no evidence of crystallisation). The filtered solution was warmed to 60-65° C. and seeded with compound [1]-L-tartrate salt form II (0.003 g) prepared in accordance with Example 5 of WO 2011/089401 (Cyclacel Limited). The mixture was stirred at 60-65° C. for 1 hour during which time crystallisation initiated. The suspension was then cooled to 15-20° C. at 10° C./h. After stirring at 15-20° C. for 1 hour, the solid was filtered, washed with ethanol (3×60 mL) and pulled dry. Further drying in a vacuum oven yielded [1]-L-tartrate salt as a white solid (36.0 g, 87% from free base). $^1$H NMR confirmed the identity of the product and HPLC (Method B) indicated a purity of 98.80%. The product was also analysed by chiral HPLC. DSC analysis (peak 182.73° C., onset 179.61° C.) and XRPD confirmed form II in accordance with WO 2011/089401 (see Table 2 for reference XRPD peaks).

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

TABLE 1

XRPD peaks for crystalline free base (Form A) of compound [1]

| Pos. [°2Th.] | Height [cts] | FWHM [°2Th.] | d-spacing [Å] | Rel. Int. [%] | Tip width [°2Th.] |
|---|---|---|---|---|---|
| 7.5313 | 21162.64 | 0.0768 | 11.73852 | 100.00 | 0.0921 |
| 9.6026 | 846.92 | 0.0768 | 9.21066 | 4.00 | 0.0921 |
| 10.2275 | 400.15 | 0.1023 | 8.64925 | 1.89 | 0.1228 |
| 11.2954 | 1863.94 | 0.1023 | 7.83384 | 8.81 | 0.1228 |
| 11.6652 | 300.53 | 0.1023 | 7.58631 | 1.42 | 0.1228 |
| 12.2672 | 3812.02 | 0.1023 | 7.21534 | 18.01 | 0.1228 |
| 12.6242 | 497.83 | 0.1023 | 7.01205 | 2.35 | 0.1228 |
| 13.1780 | 953.85 | 0.1023 | 6.71859 | 4.51 | 0.1228 |
| 14.0653 | 4092.77 | 0.1023 | 6.29672 | 19.34 | 0.1228 |
| 14.8535 | 1458.15 | 0.0768 | 5.96431 | 6.89 | 0.0921 |
| 15.1515 | 343.64 | 0.0768 | 5.84765 | 1.62 | 0.0921 |
| 15.5775 | 2894.50 | 0.1279 | 5.68868 | 13.68 | 0.1535 |
| 16.9914 | 2108.17 | 0.1023 | 5.21838 | 9.96 | 0.1228 |
| 17.6862 | 1501.97 | 0.1279 | 5.01490 | 7.10 | 0.1535 |
| 18.3040 | 644.51 | 0.0591 | 4.84701 | 3.05 | 0.0709 |
| 18.3954 | 1212.49 | 0.0768 | 4.82314 | 5.73 | 0.0921 |
| 18.6301 | 1666.18 | 0.1023 | 4.76289 | 7.87 | 0.1228 |
| 18.9784 | 1639.81 | 0.1279 | 4.67626 | 7.75 | 0.1535 |
| 19.3292 | 475.31 | 0.1023 | 4.59219 | 2.25 | 0.1228 |
| 20.2061 | 1067.39 | 0.1023 | 4.39483 | 5.04 | 0.1228 |

TABLE 2

XRPD peaks for L-tartrate salt (Form E, also known as Form II) of compound [1]

| Pos. [°2Th.] | Height [cts] | FWHM [°2Th.] | d-spacing [Å] | Rel. Int. [%] | Tip width [°2Th.] |
|---|---|---|---|---|---|
| 6.6675 | 15483.76 | 0.0768 | 13.25733 | 100.00 | 0.0921 |
| 8.2340 | 241.15 | 0.1023 | 10.73824 | 1.56 | 0.1228 |
| 9.7722 | 479.22 | 0.1023 | 9.05118 | 3.09 | 0.1228 |
| 11.9598 | 926.89 | 0.1023 | 7.40005 | 5.99 | 0.1228 |
| 12.3792 | 494.24 | 0.0768 | 7.15029 | 3.19 | 0.0921 |
| 13.0632 | 4104.92 | 0.0768 | 6.77739 | 26.51 | 0.0921 |
| 13.3777 | 2386.00 | 0.1023 | 6.61876 | 15.41 | 0.1228 |
| 13.9359 | 413.30 | 0.0768 | 6.35490 | 2.67 | 0.0921 |
| 14.9035 | 1349.55 | 0.1023 | 5.94439 | 8.72 | 0.1228 |
| 15.4032 | 975.17 | 0.0768 | 5.75266 | 6.30 | 0.0921 |
| 15.9507 | 949.23 | 0.1023 | 5.55642 | 6.13 | 0.1228 |
| 16.2665 | 488.77 | 0.1023 | 5.44926 | 3.16 | 0.1228 |
| 16.5423 | 792.08 | 0.1023 | 5.35902 | 5.12 | 0.1228 |
| 17.3614 | 2687.54 | 0.1023 | 5.10799 | 17.36 | 0.1228 |
| 17.5690 | 1410.91 | 0.1023 | 5.04809 | 9.11 | 0.1228 |
| 17.8630 | 201.26 | 0.1023 | 4.96566 | 1.30 | 0.1228 |
| 19.6395 | 1756.56 | 0.0768 | 4.52032 | 11.34 | 0.0921 |
| 19.8636 | 777.97 | 0.0768 | 4.46982 | 5.02 | 0.0921 |
| 20.1195 | 549.42 | 0.1023 | 4.41355 | 3.55 | 0.1228 |
| 20.7288 | 1423.91 | 0.1279 | 4.28518 | 9.20 | 0.1535 |
| 21.1373 | 389.18 | 0.1279 | 4.20327 | 2.51 | 0.1535 |
| 21.5804 | 674.89 | 0.1535 | 4.11797 | 4.36 | 0.1842 |
| 22.5683 | 459.02 | 0.1535 | 3.93989 | 2.96 | 0.1842 |
| 22.9541 | 780.05 | 0.1279 | 3.87454 | 5.04 | 0.1535 |

TABLE 2-continued

XRPD peaks for L-tartrate salt (Form E, also known as Form II) of compound [1]

| Pos. [°2Th.] | Height [cts] | FWHM [°2Th.] | d-spacing [Å] | Rel. Int. [%] | Tip width [°2Th.] |
|---|---|---|---|---|---|
| 23.2869 | 904.34 | 0.1023 | 3.81992 | 5.84 | 0.1228 |
| 23.5693 | 1652.40 | 0.1535 | 3.77478 | 10.67 | 0.1842 |
| 24.0730 | 899.56 | 0.1535 | 3.69692 | 5.81 | 0.1842 |
| 24.6316 | 316.32 | 0.1791 | 3.61434 | 2.04 | 0.2149 |
| 25.2971 | 1357.36 | 0.1535 | 3.52074 | 8.77 | 0.1842 |
| 26.3772 | 346.67 | 0.1023 | 3.37898 | 2.24 | 0.1228 |
| 27.0905 | 141.69 | 0.1023 | 3.29160 | 0.92 | 0.1228 |
| 27.6723 | 474.86 | 0.1023 | 3.22371 | 3.07 | 0.1228 |
| 27.9727 | 708.87 | 0.1535 | 3.18977 | 4.58 | 0.1842 |
| 28.9051 | 262.52 | 0.1535 | 3.08896 | 1.70 | 0.1842 |
| 29.2843 | 136.18 | 0.1535 | 3.04982 | 0.88 | 0.1842 |
| 30.0801 | 73.71 | 0.1535 | 2.97092 | 0.48 | 0.1842 |
| 30.4059 | 137.17 | 0.1279 | 2.93982 | 0.89 | 0.1535 |
| 31.9006 | 27.79 | 0.1535 | 2.80541 | 0.18 | 0.1842 |
| 34.4898 | 70.18 | 0.2047 | 2.60050 | 0.45 | 0.2456 |

The invention claimed is:

1. A process for preparing a compound of formula [I],

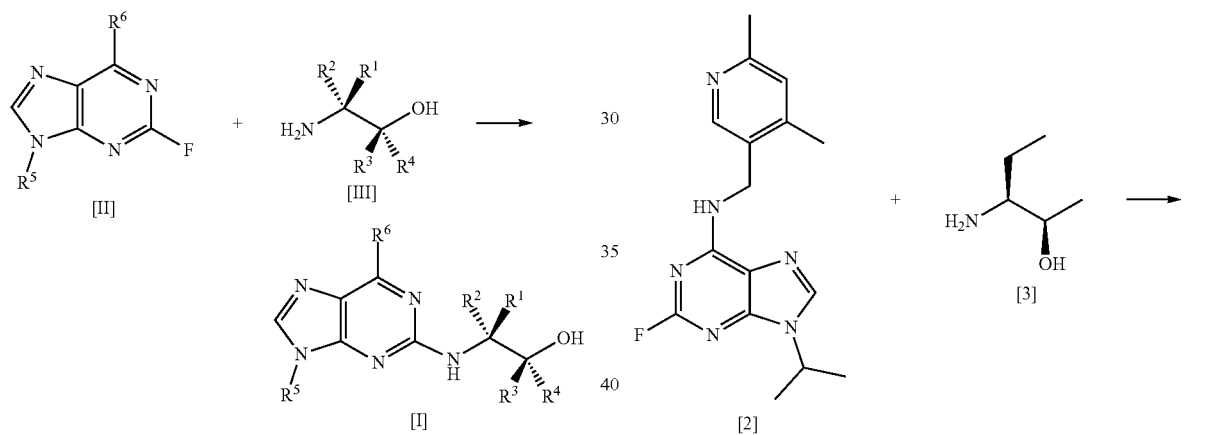

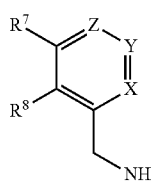

wherein:
R¹ and R² are each independently H, alkyl or haloalkyl;
R³ and R⁴ are each independently H, alkyl, haloalkyl or aryl;
R⁵ is alkyl, alkenyl, cycloalkyl or cycloalkyl-alkyl, each of which may be optionally substituted with one or more OH groups;
R⁶ is selected from cyclopropylamino, cyclopropylmethylamino, cyclobutylamino, cyclobutylmethylamino and where one of X, Y and Z is N and the remainder are CR⁹;
R⁷, R⁸ and each R⁹ are independently H, alkyl or haloalkyl, wherein at least one of R⁷, R⁸ and R⁹ is other than H;

said process comprising the steps of:
(i) forming a reaction mixture comprising (a) a compound of formula [II], (b) a compound of formula [III] and (c) 1,2-propanediol or polyethylene glycol, or a mixture thereof;
(ii) heating said reaction mixture to a temperature of at least about 150° C. to form a compound of formula [I]; and
(iii) isolating said compound of formula [I].

2. A process according to claim 1 wherein the reaction mixture in step (i) further comprises a base.

3. A process according to claim 1 wherein the reaction mixture comprises from about 2 to about 3 mole equivalents of compound [III] relative to compound [II].

4. A process according to claim 1 wherein step (iii) comprises extracting the reaction mixture from step (ii) into water and ethyl acetate, separating the ethyl acetate phase and drying with a drying agent, filtering and concentrating the filtrate.

5. A process according to claim 1 which comprises converting said compound of formula [I] into the L-tartrate salt.

6. A process according claim 1 which comprises the steps of:

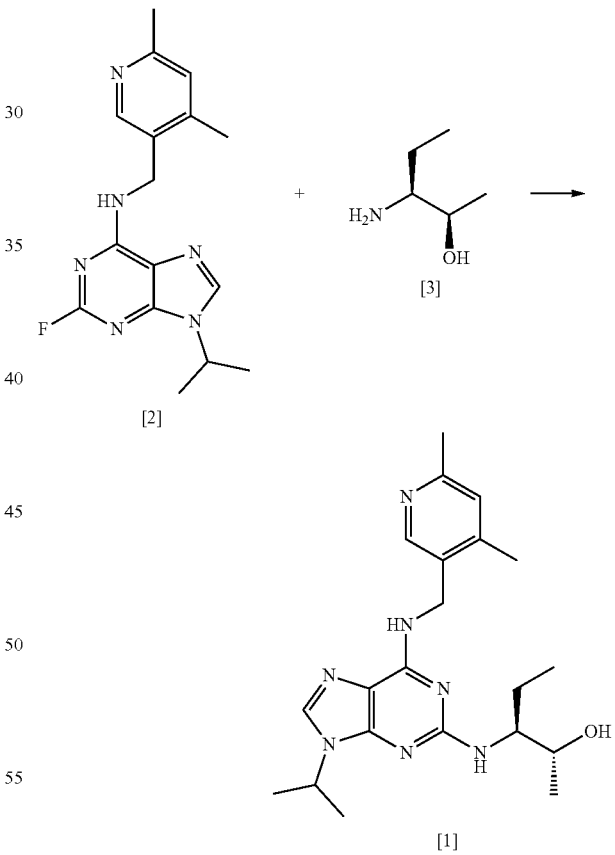

(i) forming a reaction mixture comprising (a) a compound of formula [2], (b) a compound of formula [3] and (c) 1,2-propanediol or polyethylene glycol, or a mixture thereof;
(ii) heating said reaction mixture to a temperature of at least about 150° C. to form a compound of formula [1]; and
(iii) isolating said compound of formula [1].

7. A process according to claim 6 wherein the reaction mixture in step (i) further comprises a base selected from N,N-diisopropylethylamine (DIEA), tri-$^N$propylamine, and tri-$^N$butylamine.

8. A process according to claim 6 wherein compound [2] has a purity of at least 97%.

9. A process according to claim 6 wherein compound [3] has a diastereomeric excess of at least 85%.

10. A process according to claim 1 wherein compound [III] is prepared by the steps of:

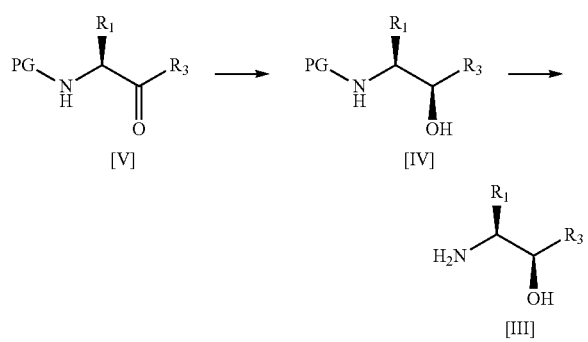

(a) treating a compound [V] with (S)-2-Me-CBS-oxazoborolidine and borane-N,N-diethylaniline complex in a solvent comprising THF to form a compound [IV]; and (b) removing the protecting group PG from said compound [IV] to give compound [III], wherein PG is a protecting group, preferably Boc, $R^1$ is alkyl or haloalkyl, and $R^3$ is alkyl, haloalkyl or aryl.

11. A process according to claim 10 which comprises the steps of:

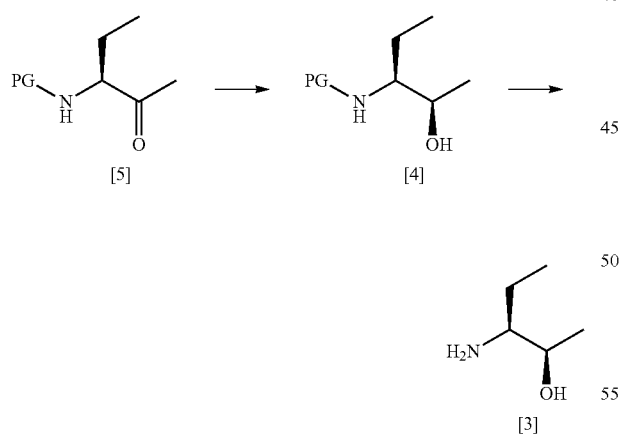

(a) treating a compound [5] with (S)-2-Me-CBS-oxazoborolidine and borane-N,N-diethylaniline complex in a solvent comprising THF to form a compound [4]; and (b) removing the protecting group PG from said compound [4] to give compound [3], where PG is a protecting group, preferably Boc.

12. A process according to claim 1 which comprises preparing a compound of formula [III] by the steps of:

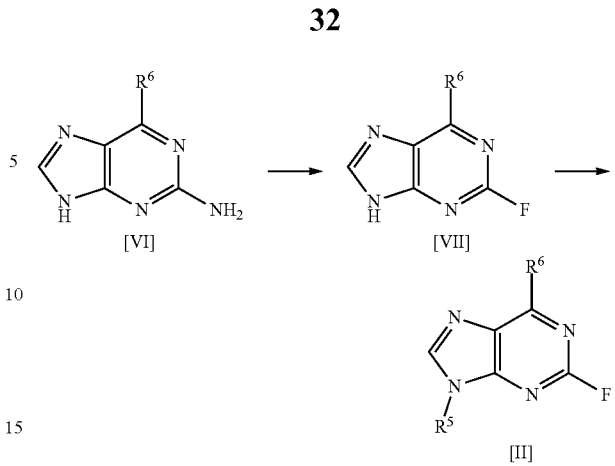

(i) treating a compound of formula [VI] with HF, pyridine and tBuONO to form a compound of formula [VII]; and (ii) treating said compound of formula [VII] with $R^5$Br in DMSO and $K_2CO_3$ to form a compound of formula [II]; where $R^5$ and $R^6$ are as defined in claim 1.

13. A process according to claim 12 which comprises the steps of:

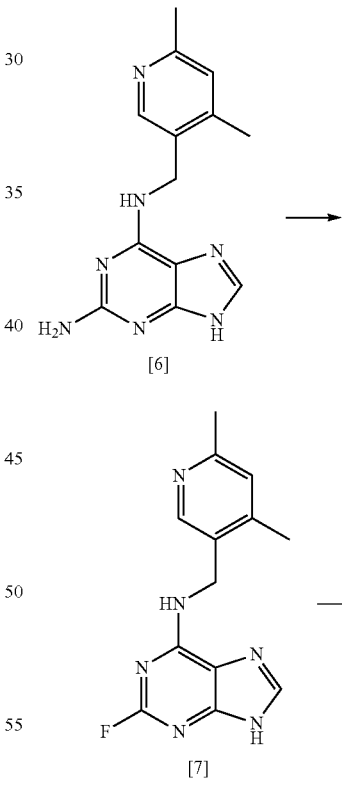

(i) treating compound [6] with HF, pyridine and $^t$BuONO to form compound [7]; and (ii) treating said compound [7] with isopropyl bromide in DMSO and $K_2CO_3$ to form compound [2].

14. A process for preparing the crystalline L-tartrate salt of compound [1], said process comprising the steps of refluxing a solution of compound [1] in ethanol and adding dropwise thereto a solution of L-tartaric acid in a mixture of water and ethanol, wherein the ratio of ethanol:water in the final mixture after addition of the L-tartaric acid solution is at least about 15:1
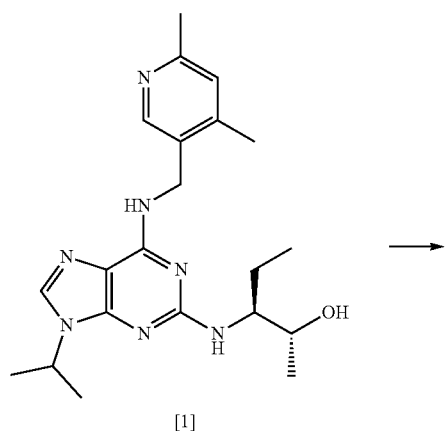
[1]
→
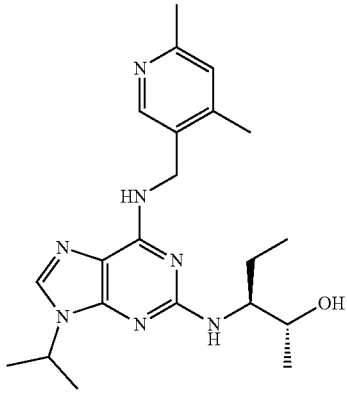 · 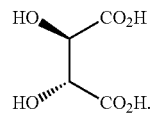
[1]-L-tartrate salt
* * * * *